(12) United States Patent
Srinivasan et al.

(10) Patent No.: US 10,524,866 B2
(45) Date of Patent: Jan. 7, 2020

(54) SYSTEMS AND METHODS FOR REGISTRATION OF LOCATION SENSORS

(71) Applicant: Auris Health, Inc., Redwood City, CA (US)

(72) Inventors: Subashini Srinivasan, San Carlos, CA (US); David Paul Noonan, San Francisco, CA (US); David Burdick Berman, Millbrae, CA (US); Brian Matthew Patenaude, Mountain View, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/365,386

(22) Filed: Mar. 26, 2019

(65) Prior Publication Data
US 2019/0298458 A1 Oct. 3, 2019

Related U.S. Application Data

(60) Provisional application No. 62/649,513, filed on Mar. 28, 2018.

(51) Int. Cl.
*G06F 19/00* (2018.01)
*A61B 34/20* (2016.01)
(Continued)

(52) U.S. Cl.
CPC .............. *A61B 34/20* (2016.02); *A61B 34/10* (2016.02); *A61B 90/361* (2016.02); *A61B 90/39* (2016.02);
(Continued)

(58) Field of Classification Search
CPC ....... A61B 34/20; A61B 34/10; A61B 90/361; A61B 90/39; A61B 2034/107;
(Continued)

(56) References Cited

U.S. PATENT DOCUMENTS

| 4,745,908 A | 5/1988 | Wardle |
| 5,273,025 A | 12/1993 | Sakiyam et al. |

(Continued)

FOREIGN PATENT DOCUMENTS

| CN | 106821498 | 6/2017 |
| EP | 3 025 630 | 6/2016 |

(Continued)

OTHER PUBLICATIONS

Ciuti et al., 2012, Intra-operative monocular 3D reconstruction for image-guided navigation in active locomotion capsule endoscopy. Biomedical Robotics and Biomechatronics (Biorob), 4th IEEE Ras & Embs International Conference on IEEE.

(Continued)

*Primary Examiner* — Harry Y Oh
(74) *Attorney, Agent, or Firm* — Knobbe, Martens, Olson & Bear, LLP

(57) ABSTRACT

Provided are systems and methods for registration of location sensors. In one aspect, a system includes an instrument and a processor configured to provide a first set of commands to drive the instrument along a first branch of the luminal network, the first branch being outside a path to a target within a model. The processor is also configured to track a set of one or more registration parameters during the driving of the instrument along the first branch and determine that the set of registration parameters satisfy a registration criterion. The processor is further configured to determine a registration between a location sensor coordinate system and a model coordinate system based on location data received from a set of location sensors during the driving of the instrument along the first branch and a second branch.

30 Claims, 26 Drawing Sheets

(51) Int. Cl.
*A61B 90/00* (2016.01)
*A61B 34/10* (2016.01)
*A61B 17/00* (2006.01)
*A61B 34/00* (2016.01)

(52) U.S. Cl.
CPC ..... *A61B 34/25* (2016.02); *A61B 2017/00809* (2013.01); *A61B 2034/107* (2016.02); *A61B 2034/2051* (2016.02); *A61B 2034/2065* (2016.02); *A61B 2034/2068* (2016.02); *A61B 2034/2074* (2016.02)

(58) Field of Classification Search
CPC .... A61B 2034/2051; A61B 2034/2065; A61B 2034/2068; A61B 2034/2074; A61B 34/25; A61B 2017/00809
See application file for complete search history.

(56) References Cited

U.S. PATENT DOCUMENTS

| | | | |
|---|---|---|---|
| 5,526,812 A | 6/1996 | Dumoulin et al. | |
| 5,550,953 A | 8/1996 | Seraji | |
| 5,831,614 A | 11/1998 | Tognazzini et al. | |
| 5,935,075 A | 8/1999 | Casscells | |
| 6,038,467 A | 3/2000 | De Bliek et al. | |
| 6,047,080 A | 4/2000 | Chen | |
| 6,059,718 A | 5/2000 | Taniguchi et al. | |
| 6,063,095 A | 5/2000 | Wang et al. | |
| 6,167,292 A | 12/2000 | Badano | |
| 6,203,493 B1 * | 3/2001 | Ben-Haim ......... A61B 1/00135 600/117 |
| 6,246,784 B1 | 6/2001 | Summers | |
| 6,246,898 B1 | 6/2001 | Vesely | |
| 6,332,089 B1 * | 12/2001 | Acker ................. A61B 5/0422 128/899 |
| 6,425,865 B1 | 7/2002 | Salcudean et al. | |
| 6,466,198 B1 | 10/2002 | Feinstein | |
| 6,553,251 B1 | 4/2003 | Landesmaki | |
| 6,665,554 B1 | 12/2003 | Charles | |
| 6,690,964 B2 | 2/2004 | Beiger et al. | |
| 6,926,709 B2 | 8/2005 | Beiger et al. | |
| 7,180,976 B2 | 2/2007 | Wink | |
| 7,386,339 B2 | 6/2008 | Strommer et al. | |
| 7,756,563 B2 | 7/2010 | Higgins | |
| 7,850,642 B2 | 12/2010 | Moll et al. | |
| 8,190,238 B2 | 5/2012 | Moll et al. | |
| 8,298,135 B2 | 10/2012 | Ito et al. | |
| 8,394,054 B2 | 3/2013 | Wallace et al. | |
| 8,821,376 B2 | 9/2014 | Tolkowsky | |
| 8,929,631 B2 | 1/2015 | Pfister et al. | |
| 9,014,851 B2 | 4/2015 | Wong et al. | |
| 9,138,129 B2 | 9/2015 | Diolaiti | |
| 9,183,354 B2 | 11/2015 | Baker et al. | |
| 9,186,046 B2 | 11/2015 | Ramamurthy et al. | |
| 9,272,416 B2 | 3/2016 | Hourtash et al. | |
| 9,289,578 B2 | 3/2016 | Walker et al. | |
| 9,459,087 B2 | 10/2016 | Dunbar | |
| 9,504,604 B2 | 11/2016 | Alvarez | |
| 9,561,083 B2 | 2/2017 | Yu et al. | |
| 9,603,668 B2 | 3/2017 | Weingarten et al. | |
| 9,622,827 B2 | 4/2017 | Yu et al. | |
| 9,629,682 B2 | 4/2017 | Wallace et al. | |
| 9,636,184 B2 | 5/2017 | Lee et al. | |
| 9,710,921 B2 | 7/2017 | Wong et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,046,140 B2 | 8/2018 | Kokish et al. | |
| 10,080,576 B2 | 9/2018 | Romo et al. | |
| 10,123,755 B2 | 11/2018 | Walker et al. | |
| 10,130,345 B2 | 11/2018 | Wong et al. | |
| 10,136,950 B2 | 11/2018 | Schoenefeld | |
| 10,136,959 B2 | 11/2018 | Mintz et al. | |
| 10,143,360 B2 | 12/2018 | Roelle et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 2001/0039421 A1 | 11/2001 | Heilbrun | |
| 2002/0077533 A1 | 6/2002 | Bieger et al. | |
| 2002/0120188 A1 | 8/2002 | Brock et al. | |
| 2003/0105603 A1 | 6/2003 | Hardesty | |
| 2003/0125622 A1 | 7/2003 | Schweikard | |
| 2003/0195664 A1 | 10/2003 | Nowlin et al. | |
| 2004/0047044 A1 | 3/2004 | Dalton | |
| 2004/0186349 A1 | 9/2004 | Ewers | |
| 2004/0263535 A1 | 12/2004 | Birkenbach et al. | |
| 2005/0027397 A1 | 2/2005 | Niemeyer | |
| 2005/0060006 A1 | 3/2005 | Pflueger | |
| 2005/0085714 A1 | 4/2005 | Foley et al. | |
| 2005/0143649 A1 | 6/2005 | Minai et al. | |
| 2005/0143655 A1 | 6/2005 | Satoh | |
| 2005/0193451 A1 | 9/2005 | Quistgaard et al. | |
| 2005/0272975 A1 | 12/2005 | McWeeney et al. | |
| 2006/0004286 A1 | 1/2006 | Chang | |
| 2006/0015096 A1 | 1/2006 | Hauck et al. | |
| 2006/0058643 A1 | 3/2006 | Florent | |
| 2006/0098851 A1 | 5/2006 | Shoham | |
| 2006/0173290 A1 | 8/2006 | Lavallee et al. | |
| 2006/0184016 A1 | 8/2006 | Glossop | |
| 2006/0209019 A1 | 9/2006 | Hu | |
| 2006/0258935 A1 | 11/2006 | Pile-Spellman et al. | |
| 2006/0258938 A1 | 11/2006 | Hoffman et al. | |
| 2007/0032826 A1 | 2/2007 | Schwartz | |
| 2007/0055128 A1 | 3/2007 | Glossop | |
| 2007/0073136 A1 | 3/2007 | Metzger | |
| 2007/0123748 A1 | 5/2007 | Meglan | |
| 2007/0135886 A1 | 6/2007 | Maschke | |
| 2007/0167801 A1 | 7/2007 | Webler et al. | |
| 2007/0208252 A1 | 9/2007 | Makower | |
| 2007/0253599 A1 | 11/2007 | White et al. | |
| 2007/0269001 A1 | 11/2007 | Maschke | |
| 2007/0299353 A1 | 12/2007 | Harlev et al. | |
| 2008/0071140 A1 | 3/2008 | Gattani | |
| 2008/0079421 A1 | 4/2008 | Jensen | |
| 2008/0103389 A1 | 5/2008 | Begelman et al. | |
| 2008/0118118 A1 | 5/2008 | Berger | |
| 2008/0123921 A1 | 5/2008 | Gielen et al. | |
| 2008/0161681 A1 | 7/2008 | Hauck | |
| 2008/0183064 A1 | 7/2008 | Chandonnet | |
| 2008/0183068 A1 | 7/2008 | Carls et al. | |
| 2008/0183188 A1 | 7/2008 | Carls et al. | |
| 2008/0201016 A1 | 8/2008 | Finlay | |
| 2008/0207997 A1 | 8/2008 | Higgins et al. | |
| 2008/0212082 A1 | 9/2008 | Froggatt et al. | |
| 2008/0218770 A1 | 9/2008 | Moll et al. | |
| 2008/0243142 A1 | 10/2008 | Gildenberg | |
| 2008/0287963 A1 | 11/2008 | Rogers et al. | |
| 2008/0306490 A1 | 12/2008 | Lakin et al. | |
| 2008/0312501 A1 | 12/2008 | Hasegawa et al. | |
| 2009/0076476 A1 | 3/2009 | Barbagli et al. | |
| 2009/0248036 A1 | 10/2009 | Hoffman et al. | |
| 2009/0259230 A1 | 10/2009 | Khadem | |
| 2009/0262109 A1 | 10/2009 | Markowitz et al. | |

(56) References Cited

U.S. PATENT DOCUMENTS

| | | |
|---|---|---|
| 2009/0295797 A1 | 12/2009 | Sakaguchi |
| 2010/0039506 A1 | 2/2010 | Sarvestani et al. |
| 2010/0041949 A1* | 2/2010 | Tolkowsky .......... A61B 1/0052 600/109 |
| 2010/0054536 A1 | 3/2010 | Huang |
| 2010/0113852 A1 | 5/2010 | Sydora |
| 2010/0125285 A1* | 5/2010 | Sewell .................. A61B 34/71 606/130 |
| 2010/0161022 A1* | 6/2010 | Tolkowsky .......... A61B 5/0044 623/1.11 |
| 2010/0161129 A1 | 6/2010 | Costa et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2011/0054303 A1 | 3/2011 | Barrick |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0065481 A1 | 3/2012 | Hunter |
| 2012/0069167 A1* | 3/2012 | Liu ....................... A61B 6/584 348/65 |
| 2012/0082351 A1* | 4/2012 | Higgins ............. A61B 1/00147 382/128 |
| 2012/0165656 A1 | 6/2012 | Montag |
| 2012/0209069 A1 | 8/2012 | Popovic |
| 2012/0215094 A1 | 8/2012 | Rahimian et al. |
| 2012/0219185 A1 | 8/2012 | Hu |
| 2012/0289783 A1* | 11/2012 | Duindam ........... A61B 1/00147 600/118 |
| 2013/0060146 A1 | 3/2013 | Yang et al. |
| 2013/0243153 A1 | 9/2013 | Sra |
| 2013/0246334 A1 | 9/2013 | Ahuja |
| 2013/0259315 A1 | 10/2013 | Angot et al. |
| 2013/0345718 A1 | 12/2013 | Crawford |
| 2014/0114180 A1 | 4/2014 | Jain |
| 2014/0148808 A1 | 4/2014 | Inkpen et al. |
| 2014/0142591 A1 | 5/2014 | Alvarez et al. |
| 2014/0180063 A1 | 6/2014 | Zhao |
| 2014/0243849 A1 | 8/2014 | Saglam |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276937 A1 | 9/2014 | Wong et al. |
| 2014/0296655 A1 | 10/2014 | Akhbardeh et al. |
| 2014/0309527 A1 | 10/2014 | Namati et al. |
| 2014/0350391 A1 | 11/2014 | Prisco et al. |
| 2014/0357984 A1 | 12/2014 | Wallace et al. |
| 2014/0364870 A1 | 12/2014 | Alvarez et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0073266 A1 | 3/2015 | Brannan |
| 2015/0141808 A1 | 5/2015 | Elhawary |
| 2015/0141858 A1 | 5/2015 | Razavi |
| 2015/0164594 A1 | 6/2015 | Romo et al. |
| 2015/0164596 A1 | 6/2015 | Romo |
| 2015/0223725 A1 | 8/2015 | Engel |
| 2015/0223897 A1 | 8/2015 | Kostrzewski et al. |
| 2015/0223902 A1 | 8/2015 | Walker et al. |
| 2015/0265368 A1 | 9/2015 | Chopra |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0313503 A1 | 11/2015 | Seibel et al. |
| 2015/0335480 A1 | 11/2015 | Alvarez et al. |
| 2016/0000520 A1 | 1/2016 | Lachmanovich |
| 2016/0001038 A1 | 1/2016 | Romo et al. |
| 2016/0008033 A1 | 1/2016 | Hawkins et al. |
| 2016/0111192 A1 | 4/2016 | Suzara |
| 2016/0199134 A1 | 7/2016 | Brown et al. |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0314710 A1 | 10/2016 | Jarc |
| 2016/0331469 A1 | 11/2016 | Hall et al. |
| 2016/0360947 A1 | 12/2016 | Iida |
| 2016/0374541 A1 | 12/2016 | Aarawal et al. |
| 2017/0007337 A1 | 1/2017 | Dan |
| 2017/0055851 A1 | 3/2017 | Al-Ali |
| 2017/0079725 A1 | 3/2017 | Hoffman |
| 2017/0079726 A1 | 3/2017 | Hoffman |
| 2017/0100199 A1 | 4/2017 | Yu et al. |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0238807 A9 | 8/2017 | Vertikov et al. |
| 2017/0258366 A1 | 9/2017 | Tupin |
| 2017/0290631 A1 | 10/2017 | Lee et al. |
| 2017/0296202 A1 | 10/2017 | Brown |
| 2017/0325896 A1* | 11/2017 | Donhowe ............. G06F 19/321 |
| 2017/0333679 A1 | 11/2017 | Jiang |
| 2017/0340396 A1 | 11/2017 | Romo et al. |
| 2017/0348067 A1 | 12/2017 | Krimsky |
| 2017/0360508 A1 | 12/2017 | Germain et al. |
| 2017/0367782 A1 | 12/2017 | Schuh et al. |
| 2018/0025666 A1 | 1/2018 | Ho et al. |
| 2018/0055582 A1 | 3/2018 | Krimsky |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0271616 A1 | 9/2018 | Schuh et al. |
| 2018/0279852 A1* | 10/2018 | Rafii-Tari ........... A61B 1/00006 |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1* | 12/2018 | Ummalaneni ......... A61B 34/20 |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0046814 A1 | 2/2019 | Senden et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1* | 4/2019 | Rafii-Tari ............... A61B 34/10 |
| 2019/0110843 A1 | 4/2019 | Ummalaneni et al. |
| 2019/0117176 A1 | 4/2019 | Walker et al. |
| 2019/0117203 A1 | 4/2019 | Wong et al. |
| 2019/0151148 A1 | 4/2019 | Alvarez et al. |
| 2019/0228528 A1 | 4/2019 | Mintz et al. |
| 2019/0125164 A1 | 5/2019 | Roelle et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |

(56) References Cited

U.S. PATENT DOCUMENTS

| | | |
|---|---|---|
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |

FOREIGN PATENT DOCUMENTS

| | | |
|---|---|---|
| KR | 10-2014-0009359 | 1/2014 |
| WO | WO 09-097461 | 6/2007 |
| WO | WO 15/089013 | 6/2015 |
| WO | WO 17/066108 | 4/2017 |
| WO | WO 17/167754 | 10/2017 |

OTHER PUBLICATIONS

Fallavollita et al., 2010, Acquiring multiview C-arm images to assist cardiac ablation procedures, EURASIP Journal on Image and Video Processing, vol. 2010, Article ID 871408, pp. 1-10.

Haigron et al., 2004, Depth-map-based scene analysis for active navigation in virtual angioscopy, IEEE Transactions on Medical Imaging, 23(11):1380-1390.

Kumar et al., 2014, Stereoscopic visualization of laparoscope image using depth information from 3D model, Computer methods and programs in biomedicine 113(3):862-868.

Livatino et al., 2015, Stereoscopic visualization and 3-D technologies in medical endoscopic teleoperation, IEEE.

Luo et al., 2010, Modified hybrid bronchoscope tracking based on sequential monte carlo sampler: Dynamic phantom validation, Asian Conference on Computer Vision. Springer, Berlin, Heidelberg.

Mayo Clinic, Robotic Surgery, https://www.mayoclinic.org/tests-procedures/robotic-surgery/about/pac-20394974?p=1, downloaded from the internet on Jul. 12, 2018, 2 pp.

Mourgues et al., 2002, Flexible calibration of actuated stereoscopic endoscope for overlay inrobot assisted surgery, International Conference on Medical Image Computing and Computer-Assisted Intervention. Springer, Berlin, Heidelberg.

Nadeem et al., 2016, Depth Reconstruction and Computer-Aided Polyp Detection in Optical Colonoscopy Video Frames, arXiv preprint arXiv:1609.01329.

Point Cloud, Sep. 10, 2010, Wikipedia, 2 pp.

Racadio et al., Dec. 2007, Live 3D guidance in the interventional radiology suite, AJR, 189:W357-W364.

Sato et al., 2016, Techniques of stapler-based navigational thoracoscopic segmentectomy using virtual assisted lung mapping (VAL-MAP), Journal of Thoracic Disease, 8(Suppl 9):S716.

Shen et al., 2015, Robust camera localisation with depth reconstruction for bronchoscopic navigation. International Journal of Computer Assisted Radiology and Surgery, 10(6):801-813.

Solheim et al., May 14, 2009, Navigated resection of giant intracranial meningiomas based on intraoperative 3D ultrasound, Acta Neurochir, 151:1143-1151.

Song et al., 2012, Autonomous and stable tracking of endoscope instrument tools with monocular camera, Advanced Intelligent Mechatronics (AIM), 2012 IEEE-ASME International Conference on. IEEE.

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

Yip et al., 2012, Tissue tracking and registration for image-guided surgery, IEEE transactions on medical imaging 31(11):2169-2182.

Zhou et al., 2010, Synthesis of stereoscopic views from monocular endoscopic videos, Computer Vision and Pattern Recognition Workshops (CVPRW), 2010 IEEE Computer Society Conference on IEEE.

Konen et al., 1998, The VN-project: endoscopic image processing for neurosurgery, Computer Aided Surgery, 3:1-6.

Shi et al., Sep. 14-18, 2014, Simultaneous catheter and environment modeling for trans-catheter aortic valve implantation, IEEE/RSJ International Conference on Intelligent Robots and Systems, pp. 2024-2029.

Vemuri et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. <hal-01230752>.

Wilson et al., 2008, a buyer's guide to electromagnetic tracking systems for clinical applications, Proc. of SPCI, 6918:69182B-1 p. 6918B-11.

International search report and written opinion dated Jun. 19, 2019 for PCT/US2019/24147.

* cited by examiner

SYSTEMS AND METHODS FOR REGISTRATION OF LOCATION SENSORS

CROSS-REFERENCE TO RELATED APPLICATION

This application claims the benefit of U.S. Provisional Application No. 62/649,513, filed Mar. 28, 2018, which is hereby incorporated by reference in its entirety.

TECHNICAL FIELD

The systems and methods disclosed herein are directed to systems and methods for registration of location sensors, and more particularly to registering a location sensor coordinate system to another coordinate system.

BACKGROUND

Medical procedures such as endoscopy (e.g., bronchoscopy) may involve the insertion of a medical tool into a patient's luminal network (e.g., airways) for diagnostic and/or therapeutic purposes. Surgical robotic systems may be used to control the insertion and/or manipulation of the medical tool during a medical procedure. The surgical robotic system may comprise at least one robotic arm including a manipulator assembly which may be used to control the positioning of the medical tool prior to and during the medical procedure. The surgical robotic system may further comprise location sensor(s) configured to generate location data indicative of a position of the distal end of the medical tool with respect to a location sensor coordinate system.

The surgical robotic system may further utilize a model of a luminal network of a patient, which may be defined with respect to a model coordinate system. The location sensor coordinate system may not be registered to the model coordinate system, and thus the system may perform a process to achieve registration between the location sensor coordinate system and the model coordinate system such that location data received from the location sensor(s) can be used to determine the position of the distal end of the medical tool with respect to the model.

SUMMARY

The systems, methods and devices of this disclosure each have several innovative aspects, no single one of which is solely responsible for the desirable attributes disclosed herein.

In one aspect, there is provided a system, comprising: an instrument comprising a set of one or more location sensors, the set of location sensors configured to generate location data indicative of a position of the set of location sensors in a location sensor coordinate system; a set of instrument manipulators configured to control movement of the distal end of the instrument; a set of processors; and at least one computer-readable memory in communication with the set of processors and having stored thereon a model of a luminal network of a patient, the model comprising a target within a model coordinate system and a path to the target. The memory may further have stored thereon computer-executable instructions to cause the set of processors to: provide a first set of commands to the set of instrument manipulators to drive the instrument along a first branch of the luminal network, the first branch being outside the path to the target, track a set of one or more registration parameters during the driving of the instrument along the first branch; determine that the set of registration parameters satisfy a registration criterion, provide a second set of commands to the set of instrument manipulators to return the instrument back to the path and to drive the instrument along a second branch, the second branch being part of the path to the target; and determine a registration between the location sensor coordinate system and the model coordinate system based on the location data received from the set of location sensors during the driving of the instrument along the first branch and the second branch.

In another aspect, there is provided a non-transitory computer readable storage medium having stored thereon instructions that, when executed, cause at least one computing device to: provide a first set of commands to a set of instrument manipulators to drive an instrument along a first branch of a luminal network, the instrument comprising a set of one or more location sensors, the set of location sensors configured to generate location data indicative of a position of the set of location sensors in a location sensor coordinate system, the set of instrument manipulators configured to control movement of the distal end of the instrument, a memory having stored thereon a model of a luminal network of a patient, the model comprising a target within a model coordinate system and a path to the target, the first branch being outside the path to the target; track a set of one or more registration parameters during the driving of the instrument along the first branch; determine that the set of registration parameters satisfy a registration criterion; provide a second set of commands to the set of instrument manipulators to return the instrument back to the path and to drive the instrument along a second branch, the second branch being part of the path to the target; and determine a registration between the location sensor coordinate system and the model coordinate system based on the location data received from the set of location sensors during the driving of the instrument along the first branch and the second branch.

In yet another aspect, there is provided a method of registering a set of one or more location sensors, comprising: providing a first set of commands to a set of instrument manipulators to drive an instrument along a first branch of a luminal network, the instrument comprising the set of location sensors, the set of location sensors configured to generate location data indicative of a position of the set of location sensors in a location sensor coordinate system, the set of instrument manipulators configured to control movement of the distal end of the instrument, a memory having stored thereon a model of a luminal network of a patient, the model comprising a target within a model coordinate system and a path to the target, the first branch being outside the path to the target; tracking a set of one or more registration parameters during the driving of the instrument along the first branch; determining that the set of registration parameters satisfy a registration criterion, providing a second set of commands to the set of instrument manipulators to return the instrument back to the path and to drive the instrument along a second branch, the second branch being part of the path to the target; and determining a registration between the location sensor coordinate system and the model coordinate system based on the location data received from the set of location sensors during the driving of the instrument along the first branch and the second branch.

In still yet another aspect, there is provided a system comprising a set of one or more processors and at least one computer-readable memory in communication with the set of processors and having stored thereon a model of a luminal network of a patient, the model comprising a target within a model coordinate system and a path to the target, the memory further having stored thereon computer-executable instructions to cause the set of processors to: provide instructions to display the luminal network via a display device, receive an indication of a location of a target within the model coordinate system; identify a first branch and a second branch in the luminal network, the first branch being outside the path to the target, the second branch being a part of the path to the target, generate a set of instructions for driving the distal end of the instrument along the first branch, back to the path from the first branch, and along the second branch, wherein location data received from a set of one or more locations sensors during the driving of the instrument according to the instructions facilitates a registration between the a location coordinate system of the location data and the model coordinate system; and determine a registration criterion for one or more registration parameters tracked during the driving of the instrument along the first branch.

In yet another aspect there is provided a non-transitory computer readable storage medium having stored thereon instructions that, when executed, cause at least one computing device to: provide instructions to display a luminal network via a display device, the luminal network being stored on the non-transitory computer readable storage medium, and the model comprising a target within a model coordinate system and a path to the target; receive an indication of a location of a target within the model coordinate system; identify a first branch and a second branch in the luminal network, the first branch being outside the path to the target, the second branch being a part of the path to the target; generate a set of instructions for driving the distal end of the instrument along the first branch, back to the path from the first branch, and along the second branch, wherein location data received from a set of one or more locations sensors during the driving of the instrument according to the instructions facilitates a registration between the a location coordinate system of the location data and the model coordinate system; and determine a registration criterion for one or more registration parameters tracked during the driving of the instrument along the first branch.

In another aspect, there is provided a method of pre-operative planning, comprising: providing instructions to display a luminal network via a display device, the luminal network being stored on the non-transitory computer readable storage medium, and the model comprising a target within a model coordinate system and a path to the target; receiving an indication of a location of a target within the model coordinate system; identifying a first branch and a second branch in the luminal network, the first branch being outside the path to the target, the second branch being a part of the path to the target; generating a set of instructions for driving the distal end of the instrument along the first branch, back to the path from the first branch, and along the second branch, wherein location data received from a set of one or more locations sensors during the driving of the instrument according to the instructions facilitates a registration between the a location coordinate system of the location data and the model coordinate system; and determining a registration criterion for one or more registration parameters tracked during the driving of the instrument along the first branch.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
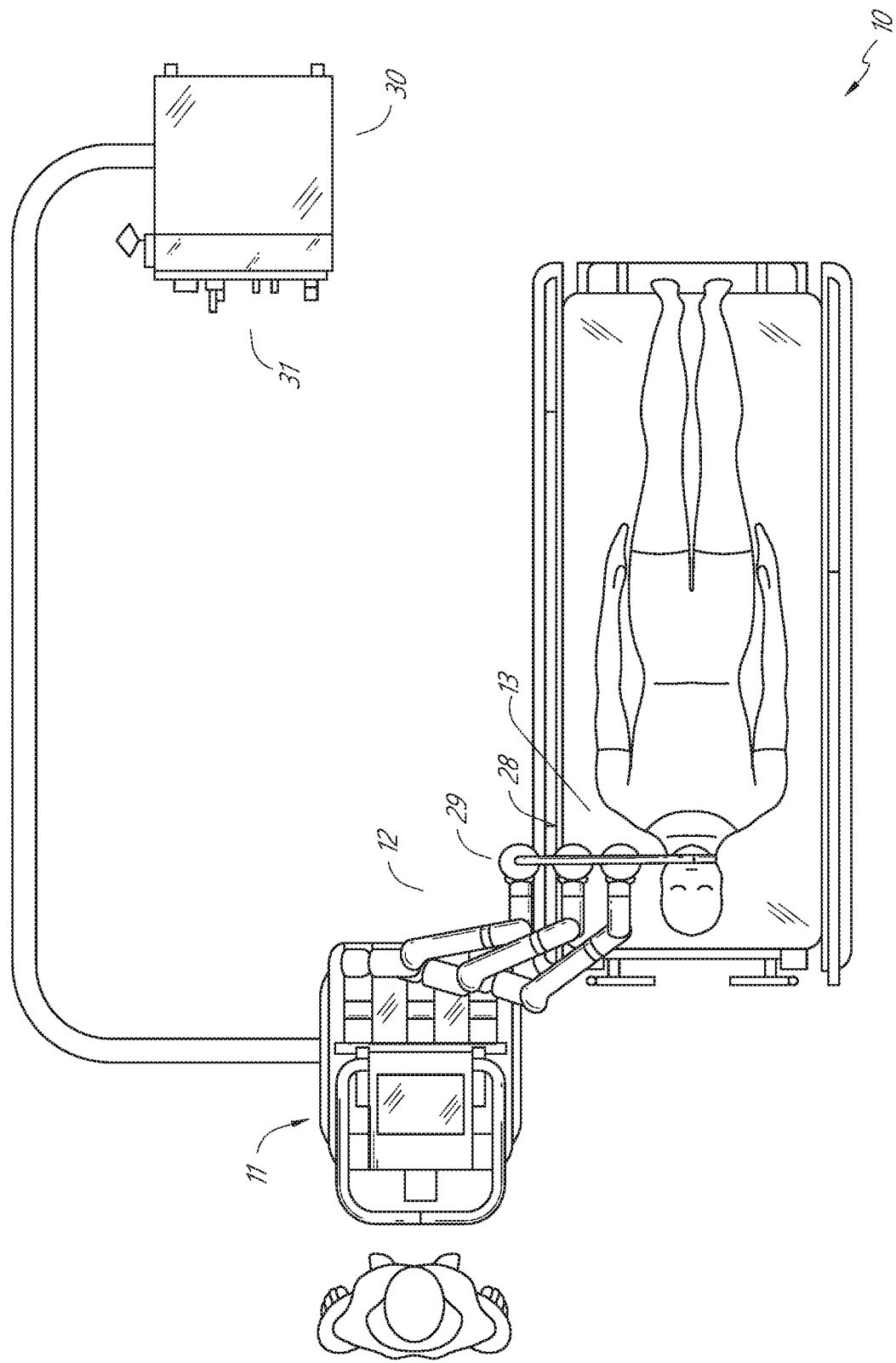
FIG. 1 illustrates an embodiment of a cart-based robotic system arranged for diagnostic and/or therapeutic bronchoscopy procedure(s).
Figure 2:
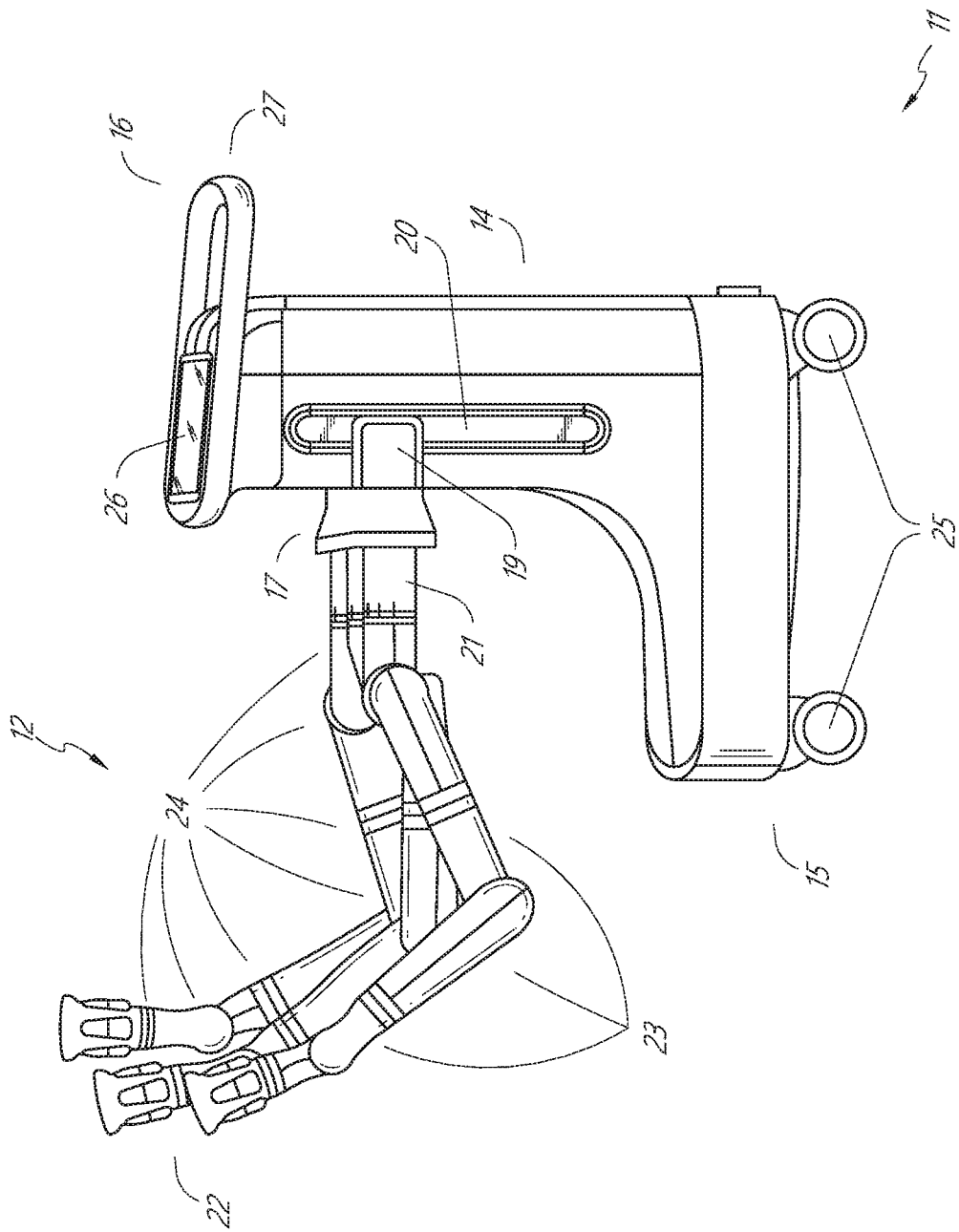
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
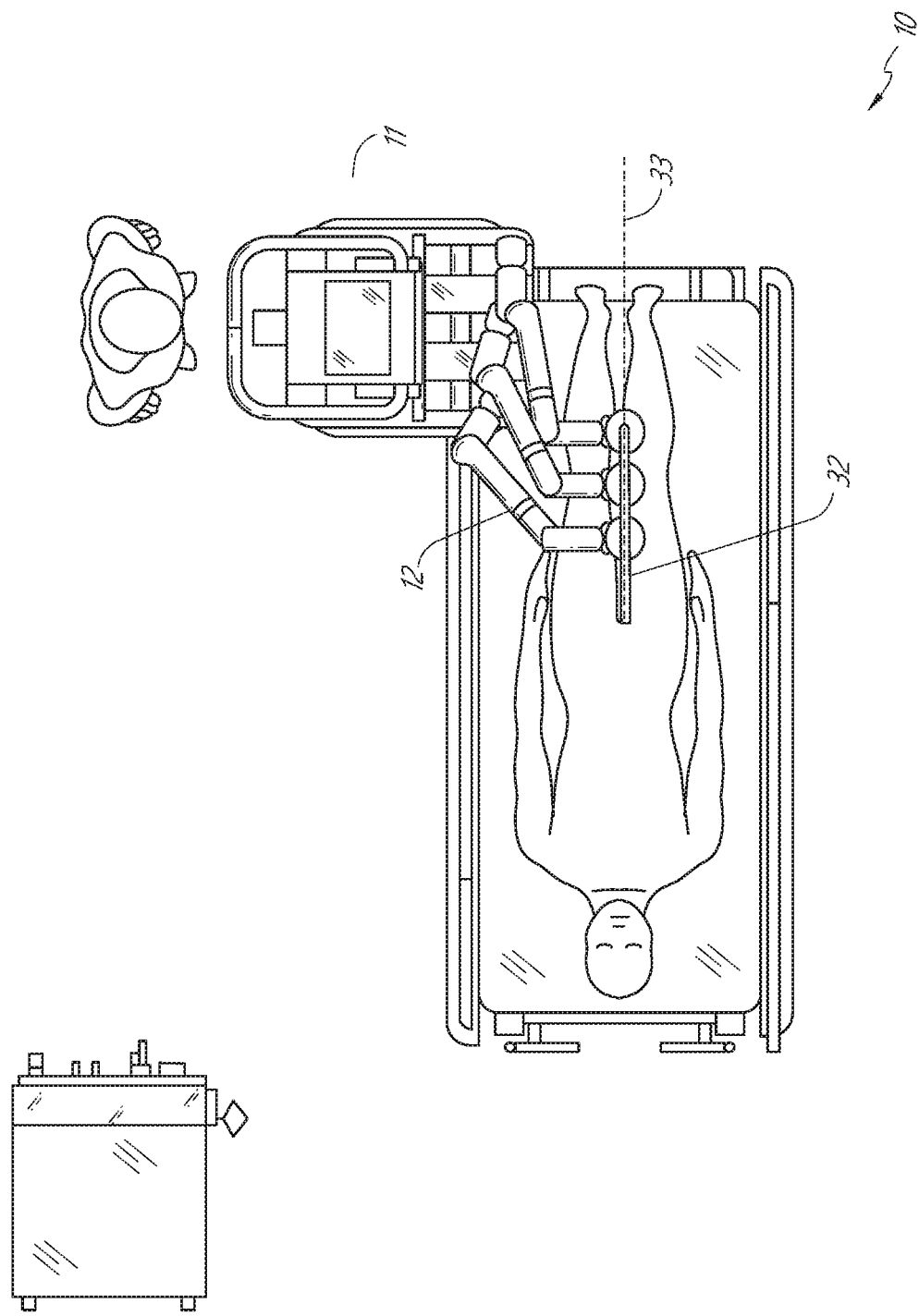
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
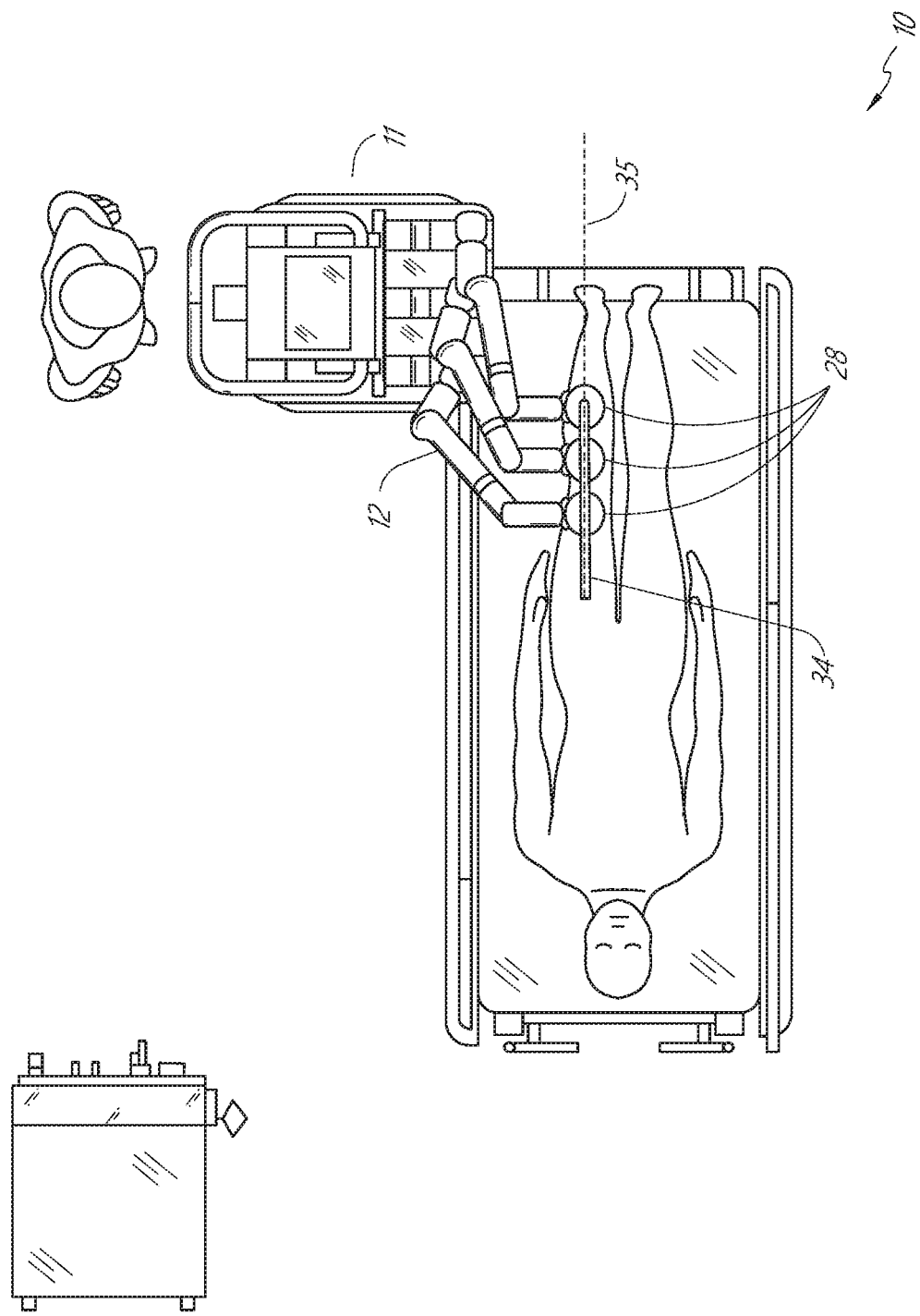
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
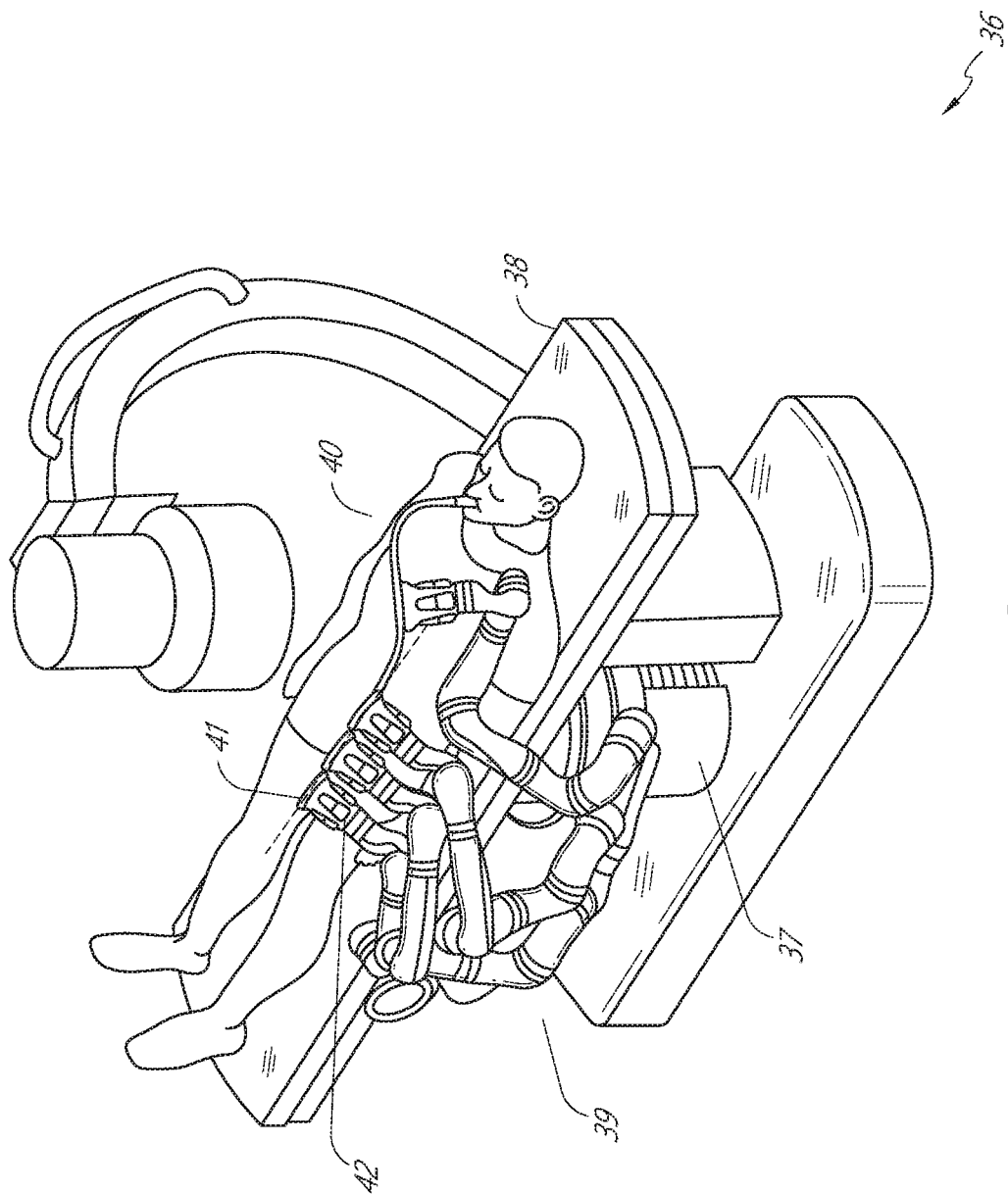
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
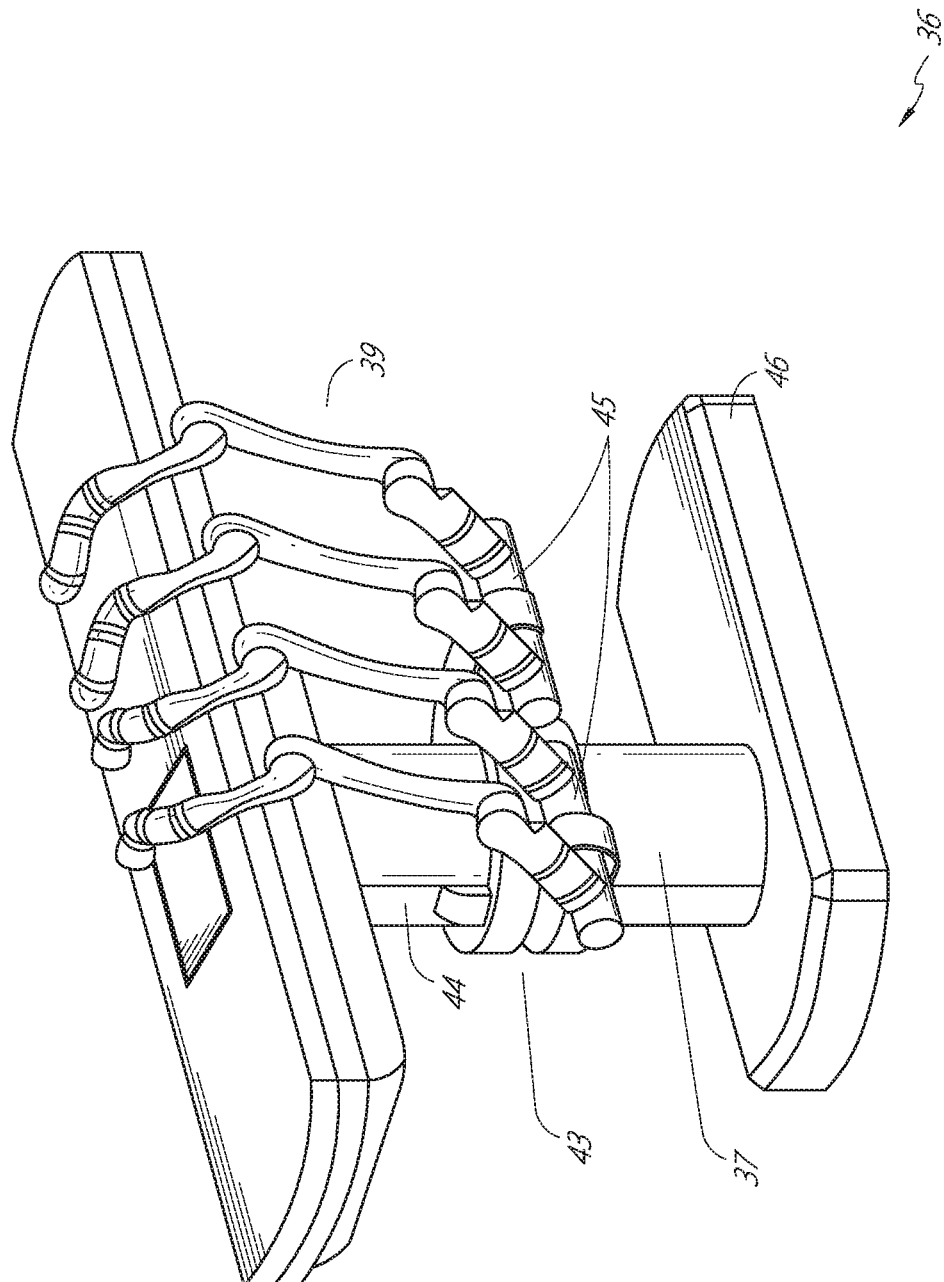
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
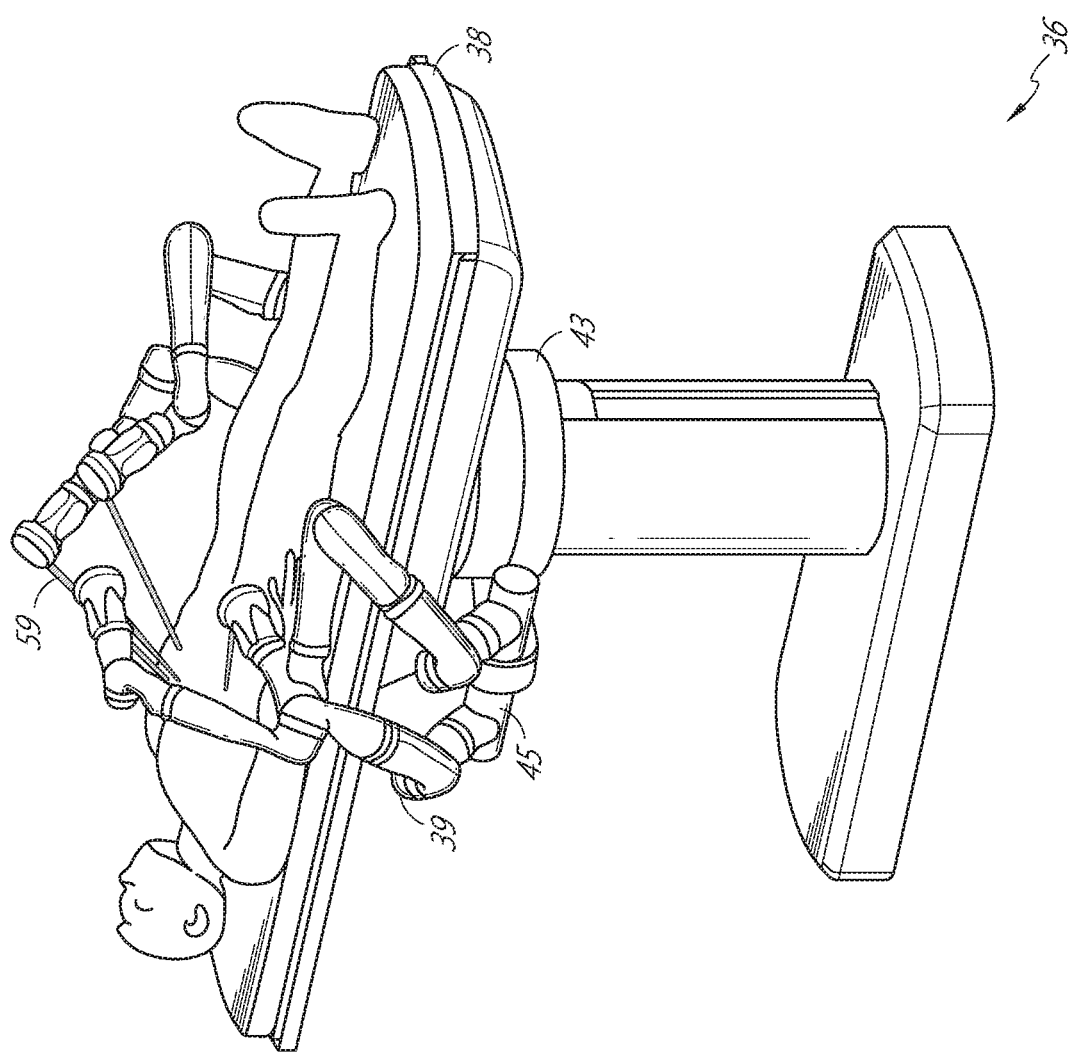
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
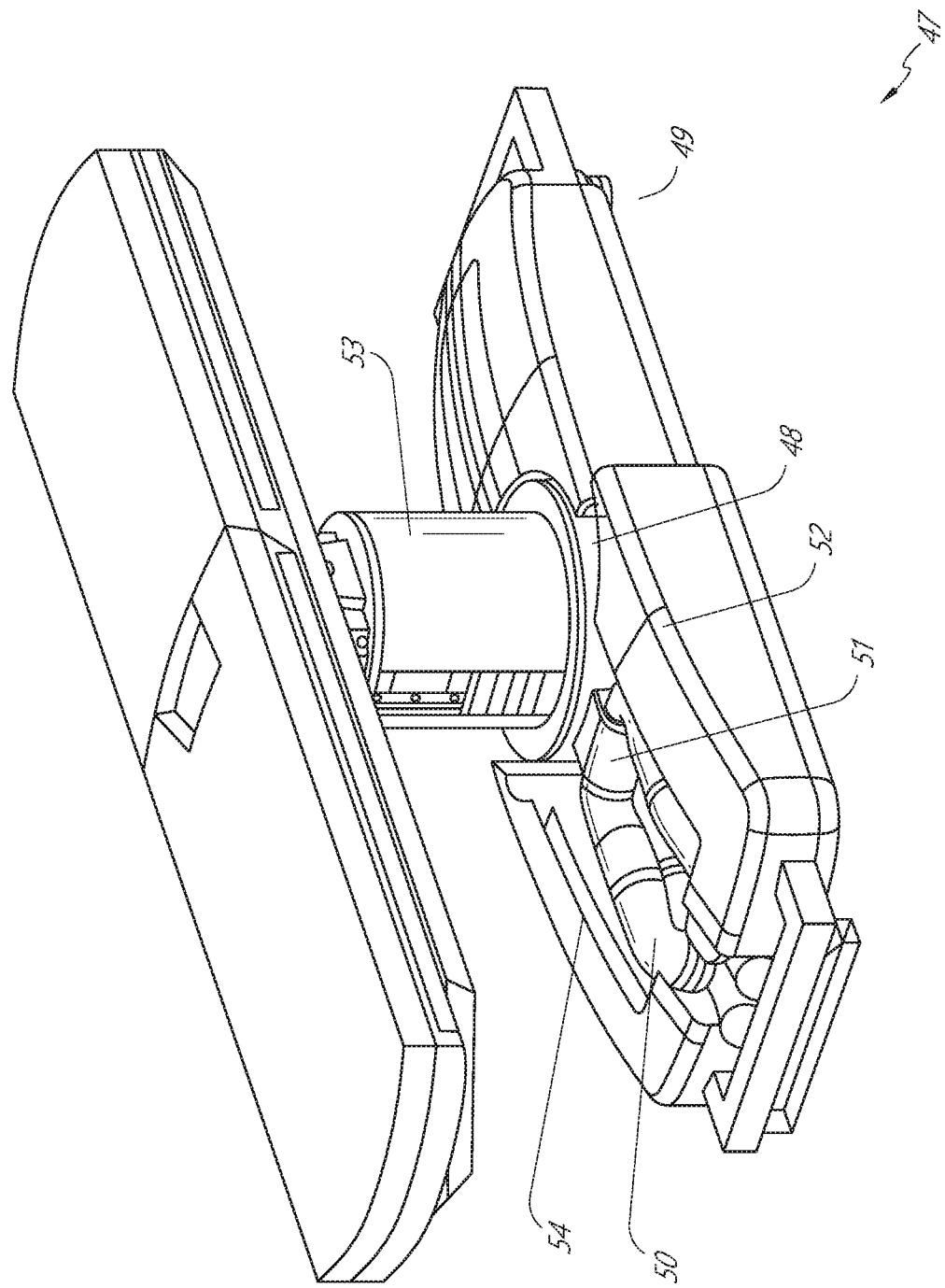
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
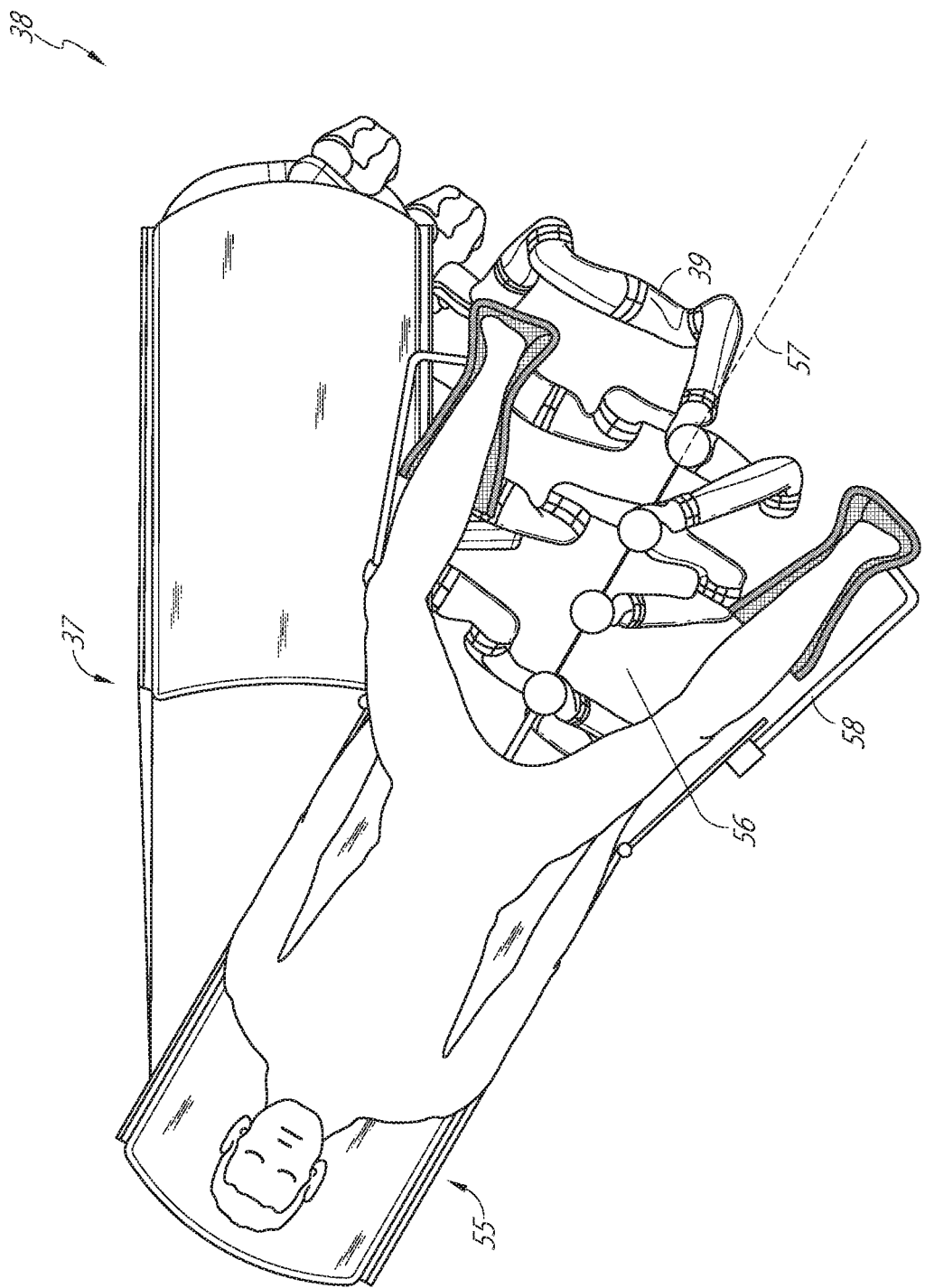
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
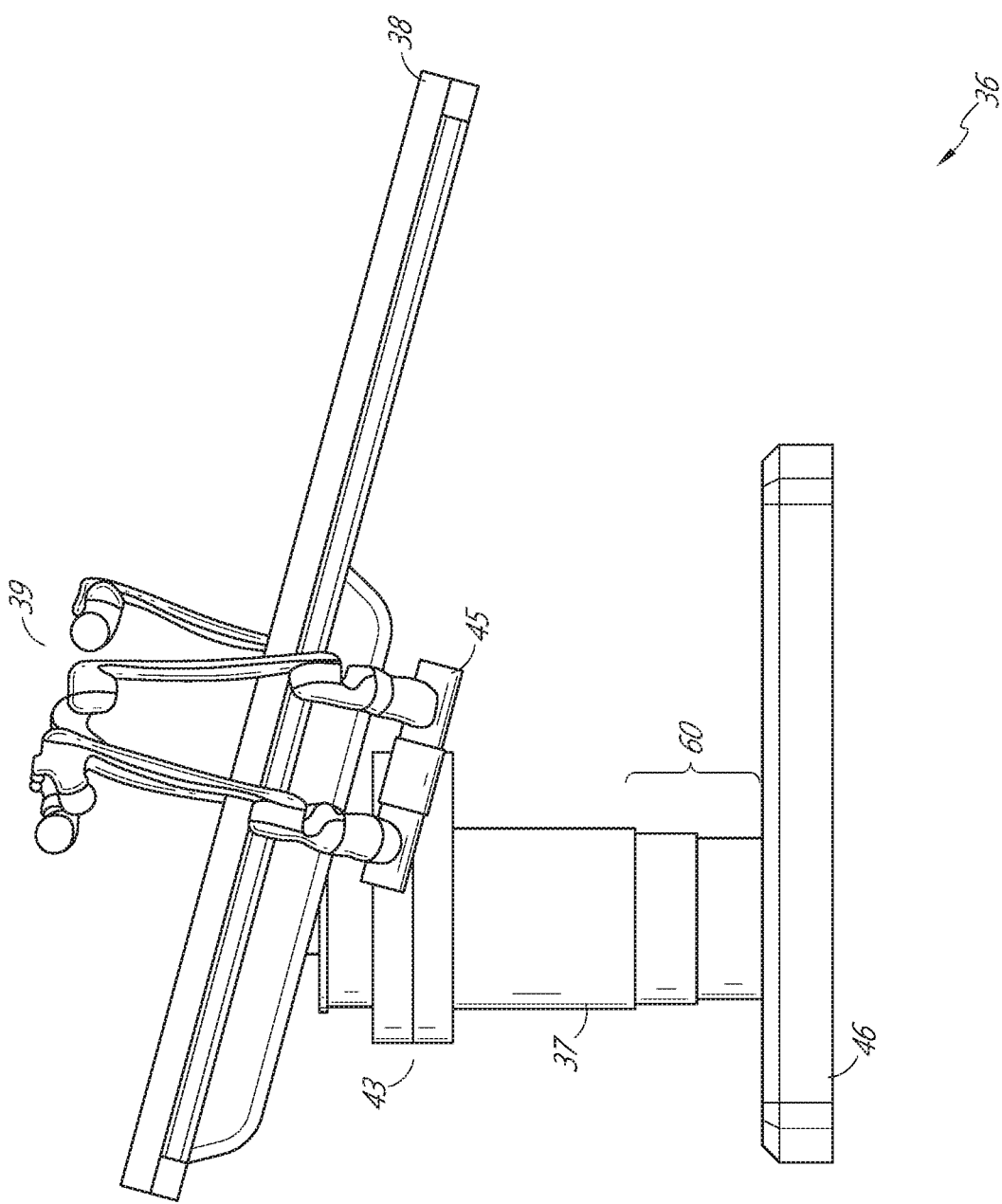
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
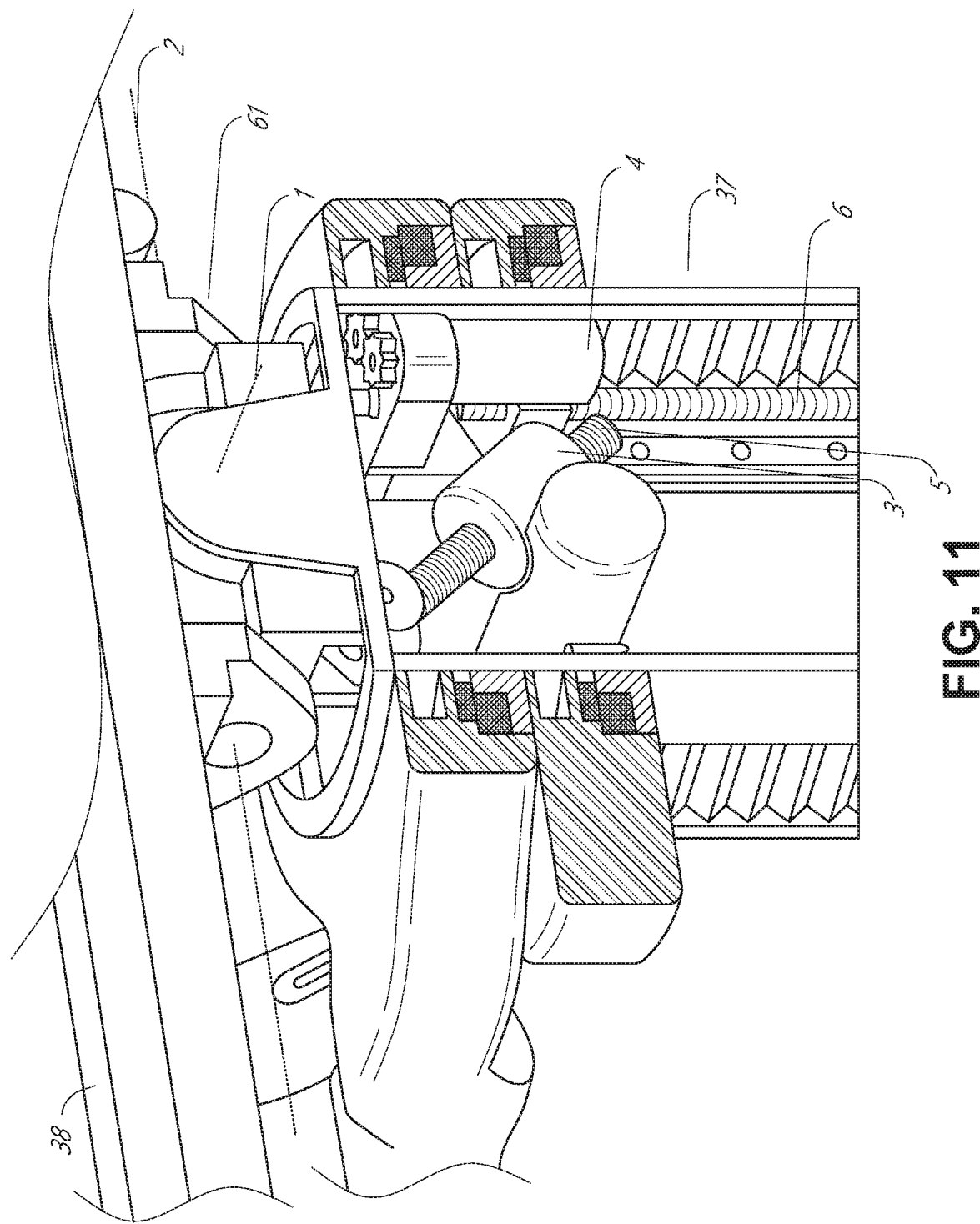
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
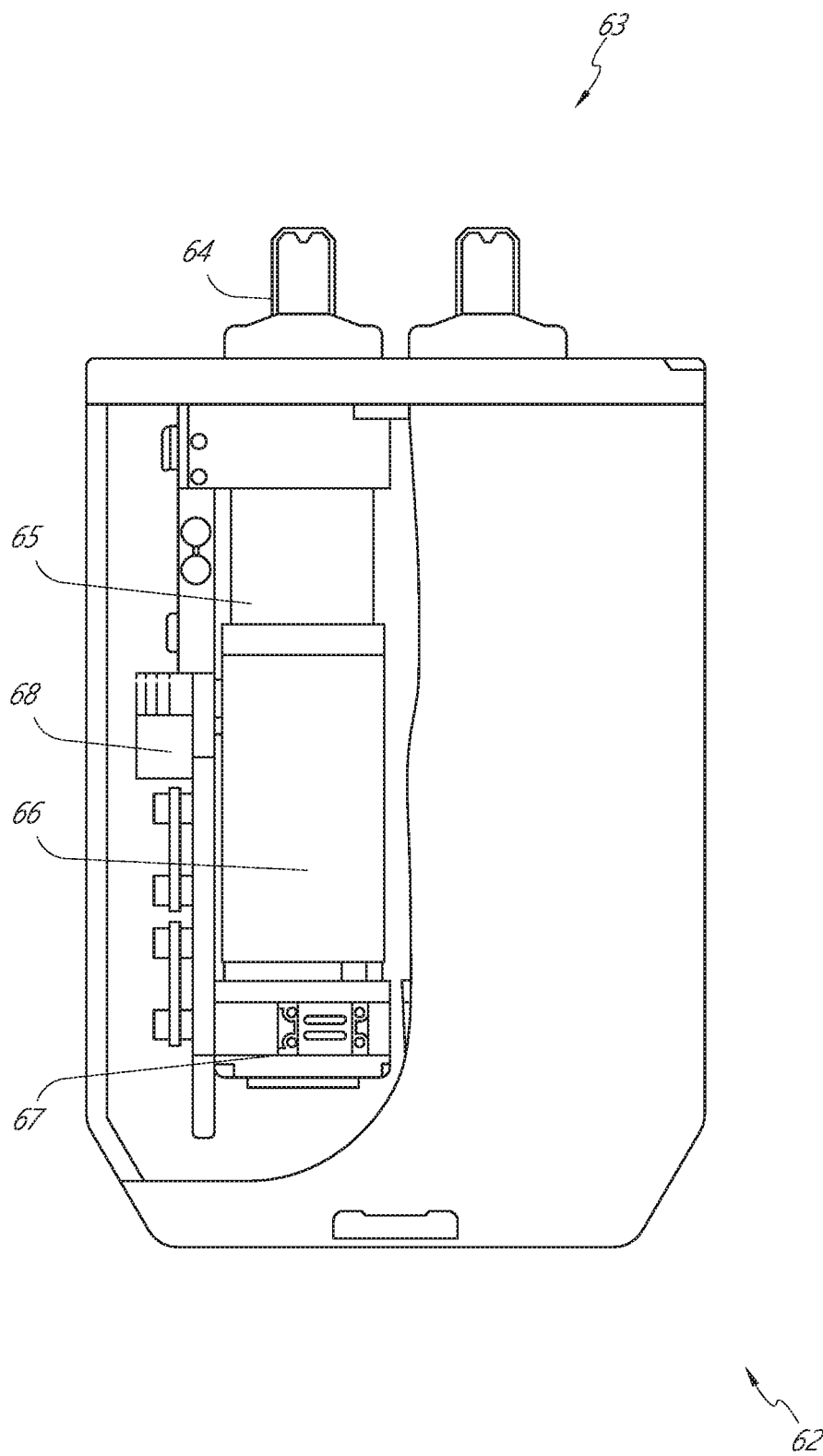
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
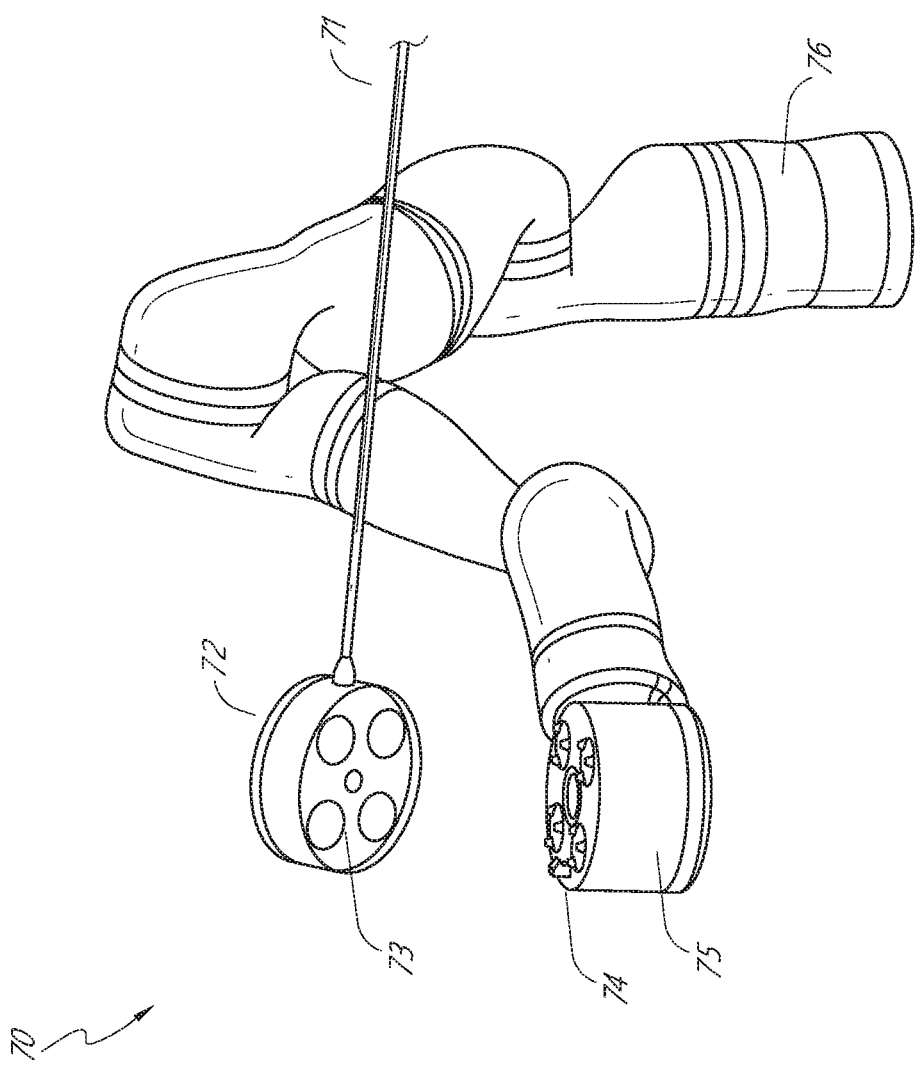
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
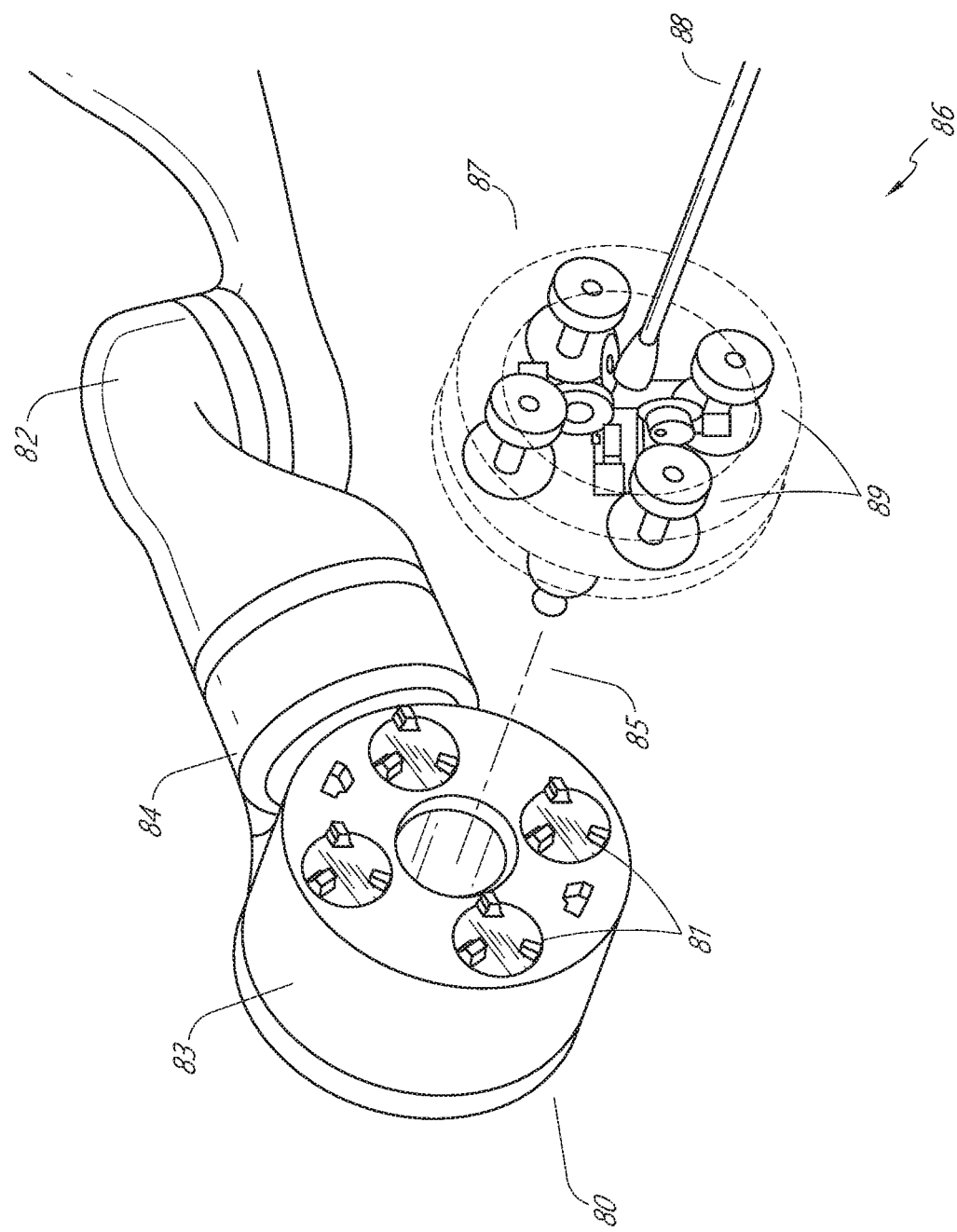
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
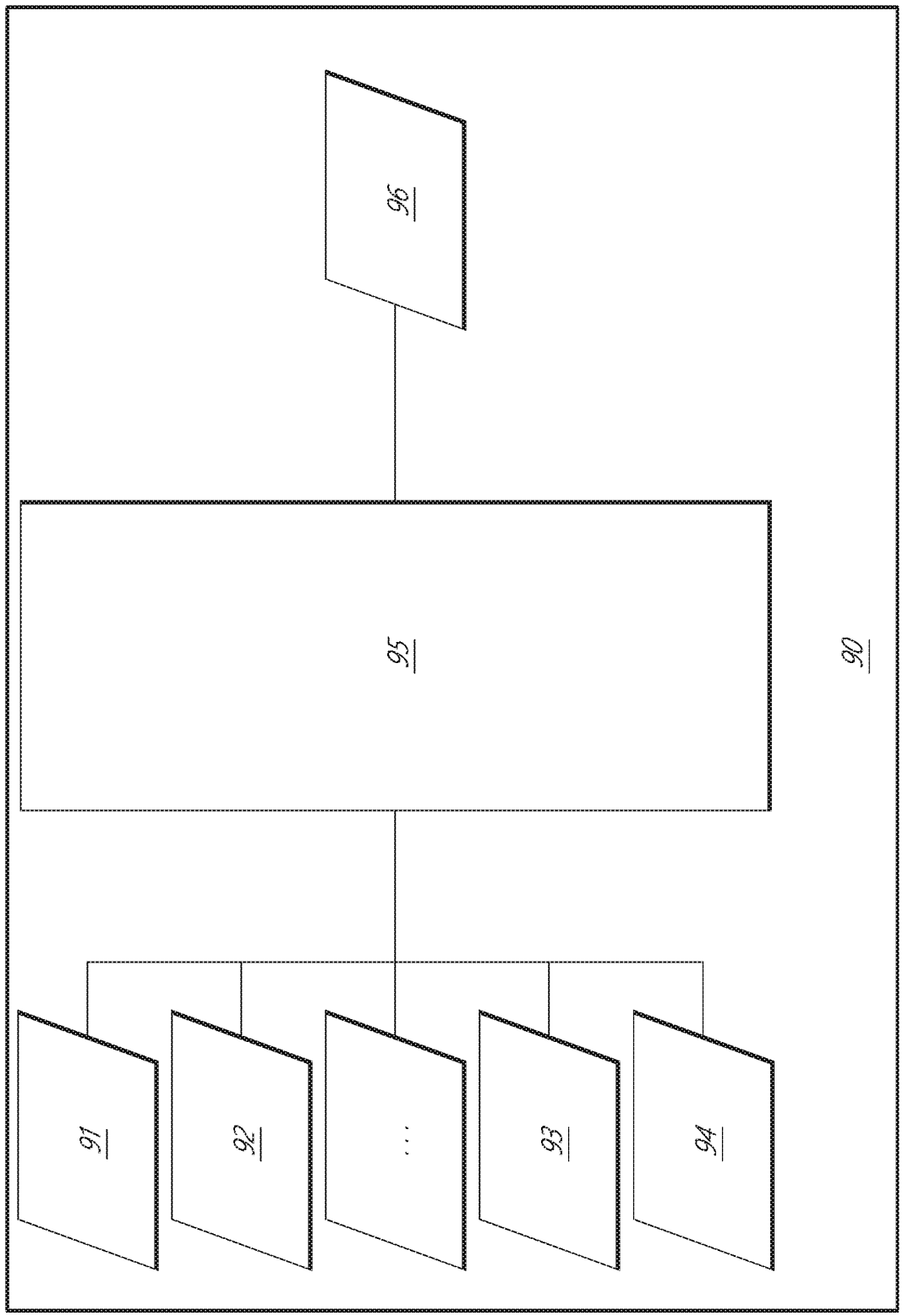
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator). The location data 96 may also be referred to herein as "state data" which describes a current state of the distal tip of the medical instrument with respect to a model (e.g., a skeletal model) of the anatomy of the patient. The state data may include information such as a position and orientation of the distal tip of the medical instrument for a given sample period. For example, when the patient's anatomy is modeled using a skeletal model based on a midpoint of the luminal network, the position may take the form of a segment ID and a depth along the segment.

The various input data 91-94 are now described in greater detail. Pre-operative mapping may be accomplished through the use of the collection of low dose CT scans. Pre-operative CT scans are reconstructed into three-dimensional (3D) images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a 3D volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Registration of Location Sensors

Embodiments of the disclosure relate to systems and techniques for registering a coordinate system used by one or more location sensors with another coordinate system, such as a coordinate system used by an anatomical model. Registration may refer to a transformation which can be applied to location sensor data to map the location sensor data into the coordinate system of the anatomical model. Thus, registration can be used by a system to determine the location of one or more location sensor(s) with respect to the anatomical model based on the location sensor data. Location sensor(s) may be used to localize the distal end of an instrument to an anatomical location during a medical procedure. The location sensor(s) may be positioned at or near the distal end of the instrument or may be positioned remote from the distal end of the instrument. Examples of location sensors which may be positioned at or near the distal end of the instrument include: EM sensors, vision-based location sensors (e.g., a camera), shape sensing fibers, etc. Examples of location sensors which may be positioned remote from the distal end of the instrument include fluoroscopic imaging devices, robotic data used to control the position of the instrument via one or more instrument manipulators, etc.

The location sensors may be configured to generate location data indicative of the location of the distal end of the instrument with respect to a location sensor coordinate system. When the location sensors are collocated with the distal end of the instrument, the location data may be representative of the location of the location sensors themselves, which can then be used to determine the location of the distal end of the instrument. In certain embodiments, the location sensor coordinate system may comprise a set of axes and an origin, which may be defined based on the particular technology used to implement the location sensors.

For example, EM sensors located in or on the instrument may be configured to measure an EM field generated by an EM field generator. The properties of the EM field, and thus, the EM values measured by the EM sensors, may be defined with respect to the location and orientation of the EM field generator. Thus, the positioning of the EM field generator may affect the values measured by the EM sensors and may also define the location and orientation of the EM coordinate system.

As described above, a patient's luminal network may be pre-operatively mapped using, for example, low dose CT scans to produce a model of the luminal network. Since the model may be produced via a different technique than used to locate the distal end of the instrument, the model coordinate system may not be aligned with the location sensor coordinate system. Accordingly, in order to use the location sensor coordinate system to track the location of the instrument with respect to the model, certain aspects of this disclosure relate to "registering" the location sensor coordinate system to the model coordinate system. This registration may include, for example, a translation and/or a rotation, which can be applied to the location data in order to map the location data from the location sensor coordinate system into the model coordinate system.

Since the model of the luminal network provides a mapping of the patient's luminal network, the model coordinate system is "anchored" or defined with respect to the patient. That is, the frame of reference for the model coordinate system is based on the location and/or orientation of the patient during the procedure. One challenge to registering the location sensor coordinate system to the model coordinate system is that the frame of reference for the location sensor coordinate system may not be "anchored" or predefined with respect to the patient. For example, when the location sensor is embodied as an EM sensor, the frame of reference for the EM coordinate system may be the EM field generator. However, in certain implementations, the EM field generator may be freely positioned within a certain area so that the EM field generator can be positioned out of the path of other elements of the robotic surgical system (e.g., robotic arms, C-arm, etc.). Since the position of the EM field generator, and thus the frame of reference of the EM coordinate system is not predefined, the system may be configured to perform a process to register the EM coordinate system to the model coordinate system.

One technique for registering the EM coordinate system to the model coordinate system may include a preoperative step of identifying a plurality of locations within the preoperative model and an intraoperative step of providing instructions to a user to drive the instrument to each of these locations. The system may instruct the user to drive the instrument to each of the locations, relying on other forms of navigation (e.g., camera feedback), and the system may further be configured to receive input from the user confirming when the instrument is located at each of the identified locations. Using the confirmations received from the user, the EM data, and the identified locations within the model, the system may determine a registration that maps the EM data to the identified locations. This registration can then be used to map the EM data representing the location of the distal end of the instrument to the model for the remainder of the procedure.

However, the above-described registration process may be complicated and time consuming for the user. For example, in order to provide a sufficiently robust registration, the system may be required to identify a relatively large number of locations (e.g., 6 or more locations) which are spatially diverse (e.g., the identified locations may be required to be at least a certain distance apart from each other). Accordingly, certain aspects of this disclosure relate to systems and techniques which may provide a registration between a location sensor coordinate system and a model coordinate system via a simplified process.

A. EM Navigation-Guided Bronchoscopy.

Hereinafter, the registration of location sensors will be described with respect to the embodiment of the registration of EM sensors for use in an EM navigation-guided bronchoscopic procedure. However, aspects of this disclosure may also apply to other location sensors which can produce location data within a corresponding location sensor coordinate system, as well as to other medical types of medical procedures.

A bronchoscope can include a light source and a small camera that allows a physician to inspect a patient's windpipe and airways. Patient trauma can occur if the precise location of the bronchoscope within the patient airways is not known. To ascertain the location of the bronchoscope, image-based bronchoscopy guidance systems can use data from the bronchoscope camera to perform local registrations (e.g., registrations at a particular location within a luminal network) at bifurcations of patient airways and so beneficially can be less susceptible to position errors due to patient breathing motion. However, as image-based guidance methods rely on the bronchoscope video, they can be affected by artifacts in bronchoscope video caused by patient coughing or mucous obstruction, etc.

EM navigation-guided bronchoscopy is a type of bronchoscopic procedure that implements EM technology to localize and guide endoscopic tools or catheters through the bronchial pathways of the lung. EM navigation-guided bronchoscopy systems can use an EM field generator that emits a low-intensity, varying EM field and establishes the position of the tracking volume around the luminal network of the patient. The EM field is a physical field produced by electrically charged objects that affects the behavior of charged objects in the vicinity of the field. EM sensors attached to the instrument when positioned within the generated field can be used to track locations and orientations of the instrument within the EM field. Small currents are induced in the EM sensors by the varying electromagnetic field. The characteristics of these electrical signals are dependent on the distance and angle between a sensor and the EM field generator. Accordingly, an EM navigation-guided bronchoscopy system can include an EM field generator, a steerable instrument having one or more EM sensors at or near its distal tip, and a guidance computing system. The EM field generator generates an EM field around the luminal network of the patient to be navigated, for example, airways, gastrointestinal tract, or a circulatory pathway. The steerable channel is inserted through the working channel of the bronchoscope and tracked in the EM field via the EM sensor.

Prior to the start of an EM navigation-guided bronchoscopy procedure, a virtual, 3D bronchial model can be obtained for the patient's specific airway structure, for example, from a preoperative CT chest scan. Using the model and an EM navigation-guided bronchoscopy system, physicians can navigate to a desired location within the lung to biopsy lesions, stage lymph nodes, insert markers to guide radiotherapy or guide brachytherapy catheters. For example, a registration can be performed at the beginning of a procedure to generate a mapping between the EM coordinate system and the model coordinate system. Thus, as the instrument is tracked during bronchoscopy, the instrument's position in the model coordinate system becomes nominally known based on position data from the EM sensor.

Figure 16A:
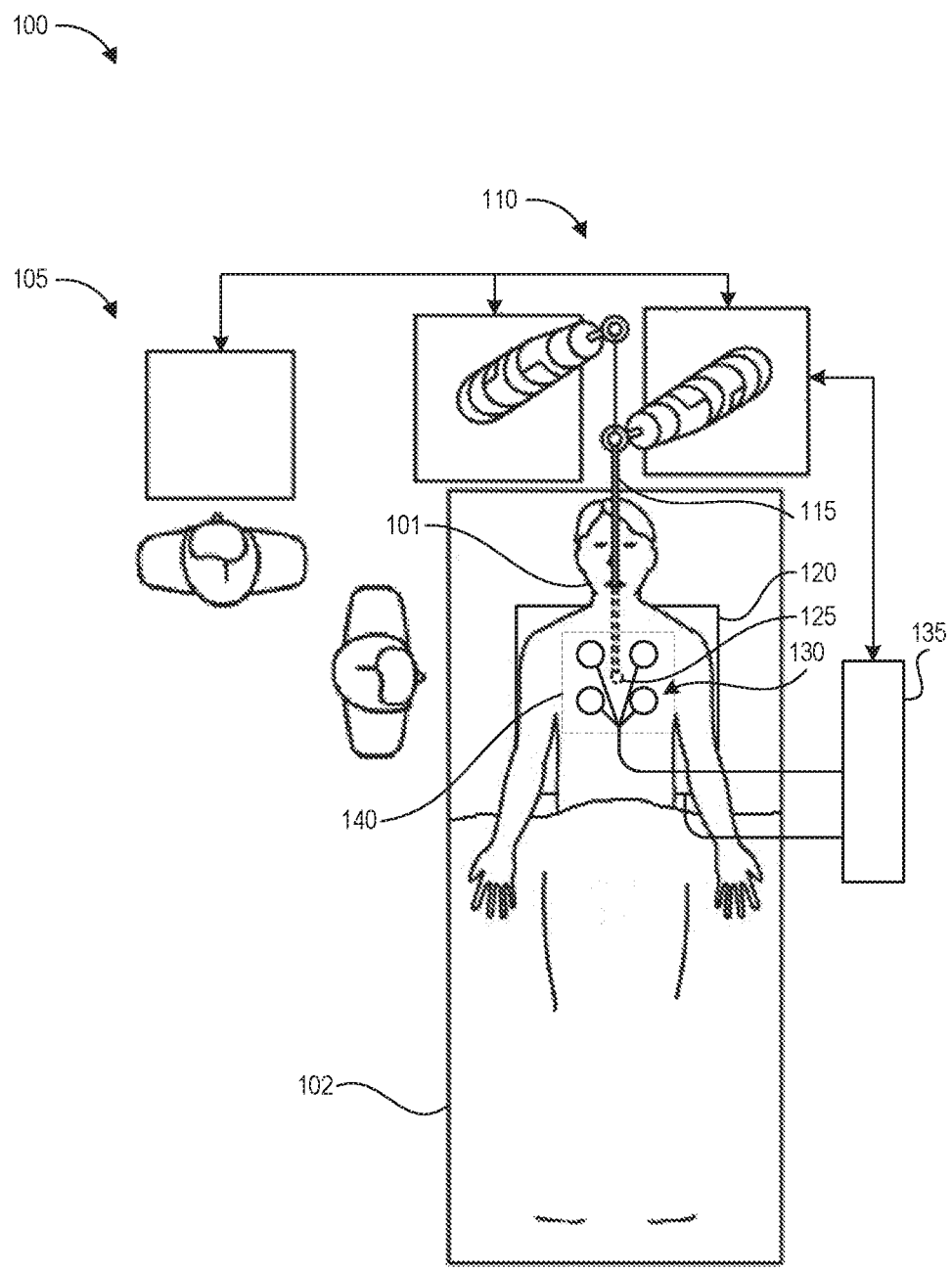
FIG. 16A illustrates an example operating environment implementing one or more aspects of the disclosed navigation systems and techniques.

FIG. 16A illustrates an example operating environment 100 implementing one or more aspects of the disclosed navigation systems and techniques. The operating environment 100 includes patient 101, a platform 102 supporting the patient 101, a surgical or medical robotic system 110 guiding movement of an instrument 115, command center 105 for controlling operations of the robotic system 110, EM controller 135, EM field generator 120, and EM sensors 125, 130. FIG. 16A also illustrates an outline of a region of a luminal network 140 within the patient 101, shown in more detail in FIG. 16B.

The system 110 can include one or more robotic arms for positioning and guiding movement of instrument 115 through the luminal network 140 of the patient 101. Command center 105 can be communicatively coupled to the robotic system 110 for receiving position data and/or providing control signals from a user. As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like. The robotic system 110 can be any of the systems described above with respect to FIGS. 1-15. An embodiment of the system 110 is discussed in more detail with respect to FIG. 16C, and the command center 105 is discussed in more detail with respect to FIG. 17.

The instrument 115 may be a tubular and flexible surgical instrument that is inserted into the anatomy of a patient to capture images of the anatomy (e.g., body tissue) and provide a working channel for insertion of other medical instruments to a target tissue site. As described above, the instrument 115 can be a procedure-specific endoscope, for example a bronchoscope, gastroscope, or ureteroscope, or may be a laparoscope or vascular steerable catheter. The instrument 115 can include one or more imaging devices (e.g., cameras or other types of optical sensors) at its distal end. The imaging devices may include one or more optical components such as an optical fiber, fiber array, photosensitive substrate, and/or lens(es). The optical components move along with the tip of the instrument 115 such that movement of the tip of the instrument 115 results in corresponding changes to the field of view of the images captured by the imaging devices. The distal end of the instrument 115 can be provided with one or more EM sensors 125 for tracking the position of the distal end within an EM field generated around the luminal network 140. The distal end of the instrument 115 is further described with reference to FIG. 18 below.

EM controller 135 can control EM field generator 120 to produce a varying EM field. The EM field can be time-varying and/or spatially varying, depending upon the embodiment. The EM field generator 120 can be an EM field generating board in some embodiments. Some embodiments of the disclosed patient navigation systems can use an EM field generator board positioned between the patient and the platform 102 supporting the patient, and the EM field generator board can incorporate a thin barrier that minimizes any tracking distortions caused by conductive or magnetic materials located below it. In other embodiments, an EM field generator board can be mounted on a robotic arm, for example, similar to those shown in the robotic system 110, which can offer flexible setup options around the patient.

Figure 16B:
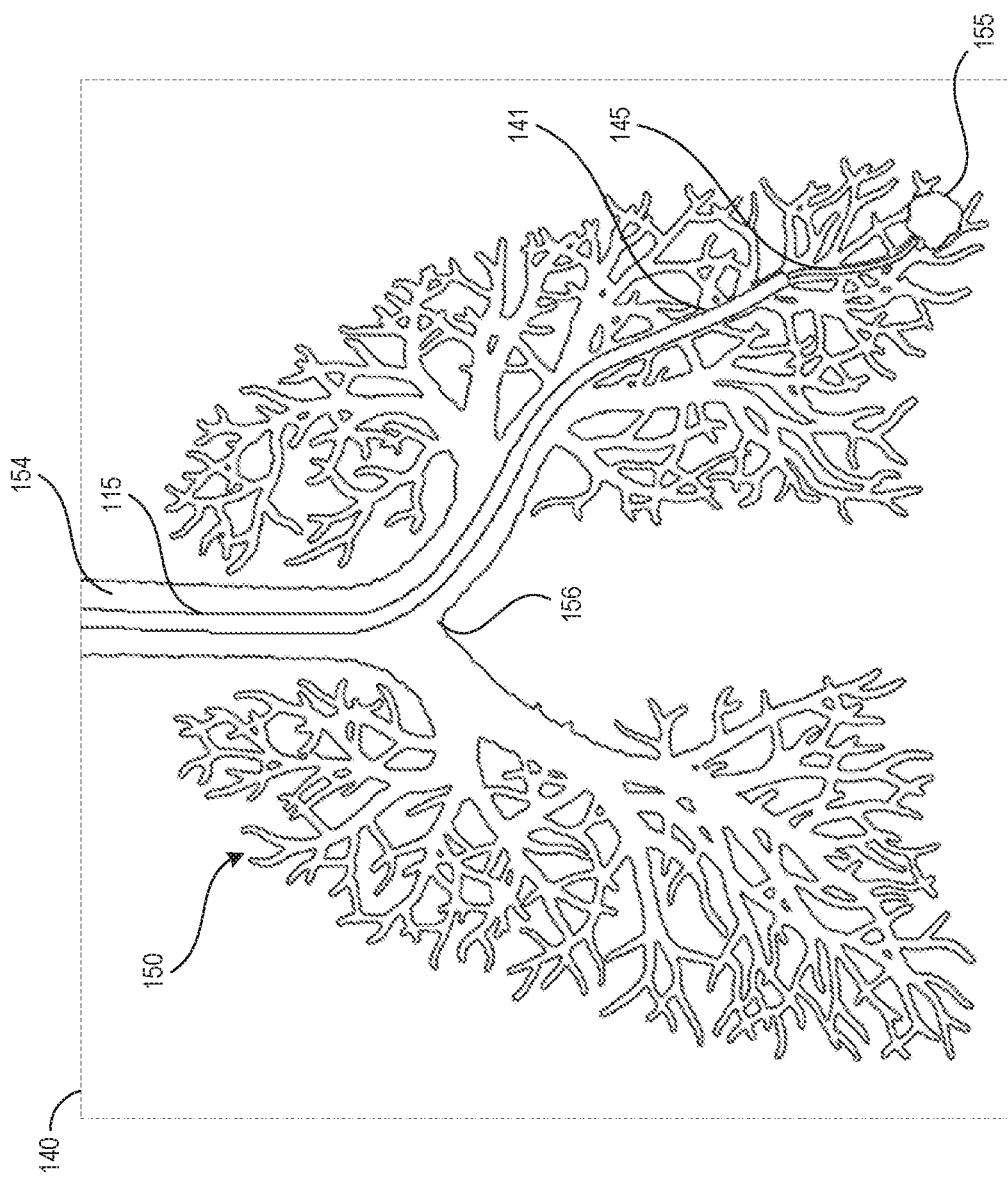
FIG. 16B illustrates an example luminal network that can be navigated in the operating environment of FIG. 16A.

FIG. 16B illustrates an example luminal network 140 that can be navigated in the operating environment 100 of FIG. 16A. The luminal network 140 includes the branched structure of the airways 150 of the patient 101, the trachea 154 leading to the main carina 156 (typically the first bifurcation encountered during bronchoscopy navigation), and a nodule (or lesion) 155 that can be accessed as described herein for diagnosis and/or treatment. As illustrated, the nodule 155 is located at the periphery of the airways 150. The instrument 115 may comprise a sheath 141 having a first diameter and thus the distal end of the sheath 141 may not able to be positioned through the smaller-diameter airways around the nodule 155. Accordingly, a scope 145 extends from the working channel of the instrument 115 and across the remaining distance to the nodule 155. The scope 145 may have a lumen through which instruments, for example, biopsy needles, cytology brushes, and/or tissue sampling forceps, can be passed to the target tissue site of nodule 155. In such implementations, both the distal end of the sheath 141 and the distal end of the scope 145 can be provided with EM sensors for tracking their respective positions within the airways 150.

In some embodiments, a 2D display of the 3D luminal network model as described herein, or a cross-section of a 3D model, can resemble FIG. 16B. Estimated position information can be overlaid onto such a representation.

Figure 16C:
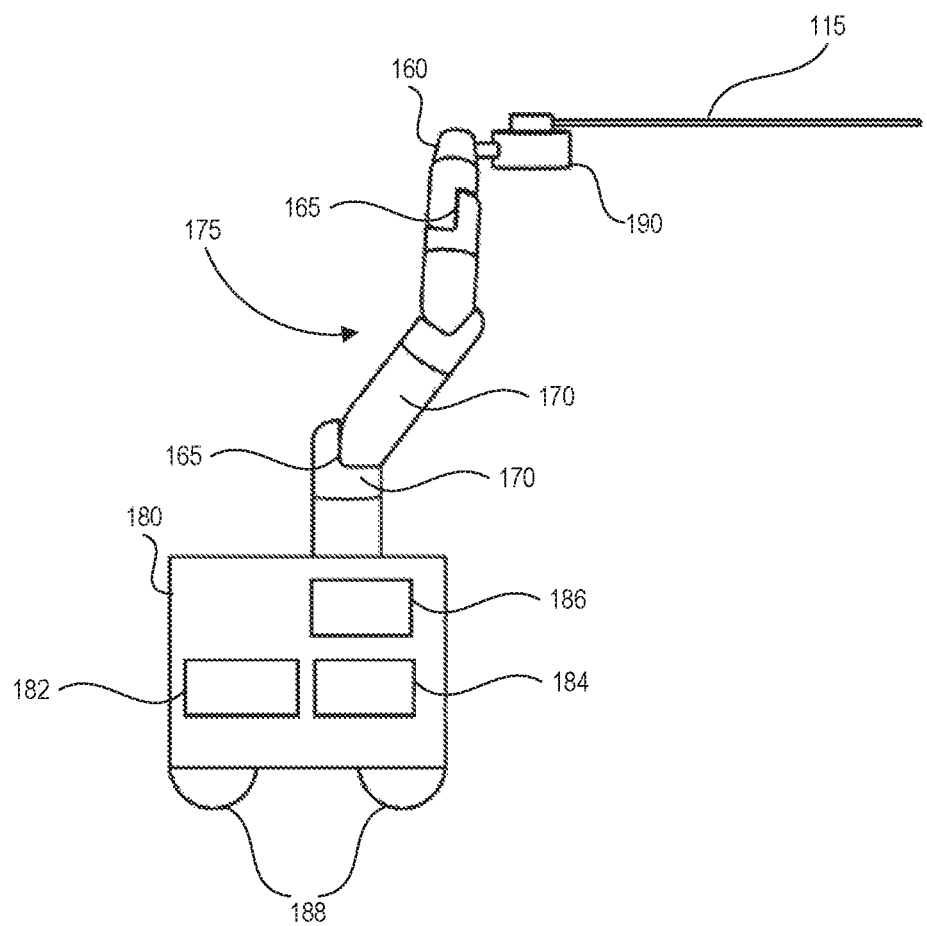
FIG. 16C illustrates an example robotic arm of a robotic system for guiding instrument movement in through the luminal network of FIG. 16B.

FIG. 16C illustrates an example robotic arm 175 of the robotic system 110 for guiding instrument movement in through the luminal network 140 of FIG. 16B. The robotic arm 175 can include robotic arms 12, 39 described above in some embodiments, and is coupled to base 180, which can include a cart base 15, column 37 of patient platform 38, or a ceiling-based mount in various embodiments. As described above, the robotic arm 175 includes multiple arm segments 170 coupled at joints 165, which provides the robotic arm 175 multiple degrees of freedom.

The robotic arm 175 may be coupled to an instrument manipulator 190, for example instrument manipulator 62 described above, e.g., using a mechanism changer interface (MCI) 160. The instrument manipulator 190 can be removed and replaced with a different type of instrument manipulator, for example, a first type of instrument manipulator configured to manipulate an endoscope or a second type of instrument manipulator configured to manipulate a laparoscope. The MCI 160 includes connectors to transfer pneumatic pressure, electrical power, electrical signals, and optical signals from the robotic arm 175 to the instrument driver 190. The MCI 160 can be a set screw or base plate connector. The instrument manipulator 190 manipulates instruments, for example, the instrument 115 using techniques including direct drive, harmonic drive, geared drives, belts and pulleys, magnetic drives, and the like. The MCI 160 is interchangeable based on the type of instrument manipulator 190 and can be customized for a certain type of surgical procedure. The robotic 175 arm can include a joint level torque sensing and a wrist at a distal end.

Robotic arm 175 of the robotic system 110 can manipulate the instrument 115 using tendons as described above to deflect the tip of the instrument 115. The instrument 115 may exhibit nonlinear behavior in response to forces applied by the elongate movement members. The nonlinear behavior may be based on stiffness and compressibility of the instrument 115, as well as variability in slack or stiffness between different elongate movement members.

The base 180 can be positioned such that the robotic arm 175 has access to perform or assist with a surgical procedure on a patient, while a user such as a physician may control the robotic system 110 from the comfort of the command console. The base 180 can be communicatively coupled to the command console 105 shown in FIG. 16A.

The base 180 can include a source of power 182, pneumatic pressure 186, and control and sensor electronics 184—including components such as a central processing unit, data bus, control circuitry, and memory—and related actuators such as motors to move the robotic arm 175. The electronics 184 can implement the navigation control techniques described herein. The electronics 184 in the base 180 may also process and transmit control signals communicated from the command console. In some embodiments, the base 180 includes wheels 188 to transport the robotic system 110 and wheel locks/brakes (not shown) for the wheels 188. Mobility of the robotic system 110 helps accommodate space constraints in a surgical operating room as well as facilitate appropriate positioning and movement of surgical equipment. Further, the mobility allows the robotic arm 175 to be configured such that the robotic arm 175 does not interfere with the patient, physician, anesthesiologist, or any other equipment. During procedures, a user may control the robotic arm 175 using control devices, for example, the command console.

Figure 17:
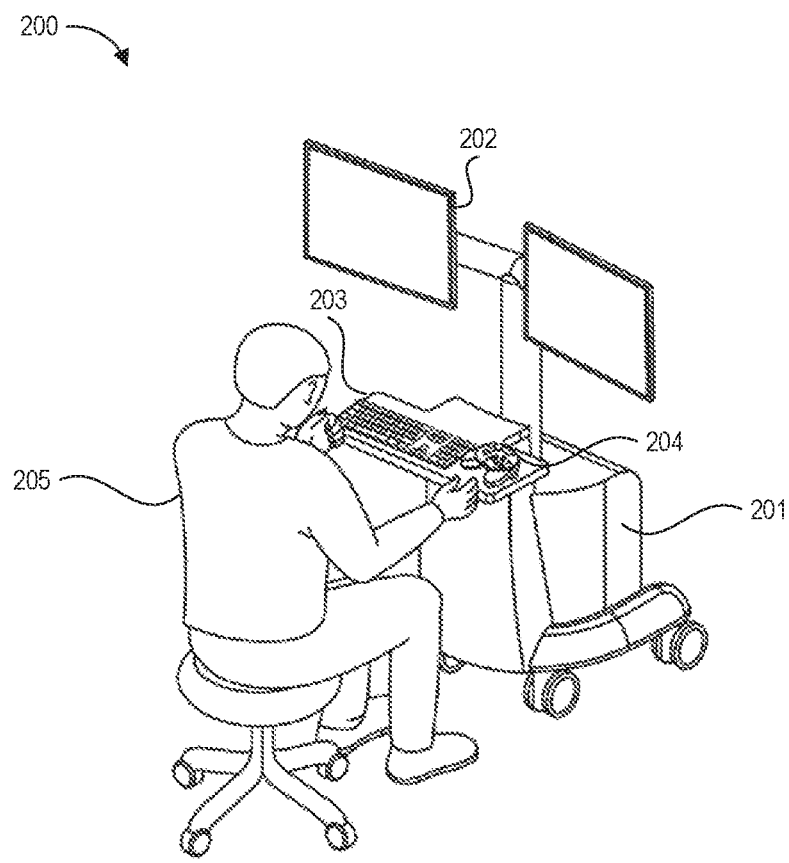
FIG. 17 illustrates an example command console that can be used, for example, as the command console in the example operating environment.

FIG. 17 illustrates an example command console 200 that can be used, for example, as the command console 105 in the example operating environment 100. The command console 200 may include a console base 201, one or more displays 202 (e.g., monitors), and one or more control modules (e.g., a keyboard 203 and joystick 204). In some embodiments, one or more of the command console 200 functionality may be integrated into a base 180 of the robotic system 110 or another system communicatively coupled to the robotic system 110. A user 205, e.g., a physician, remotely controls the robotic system 110 from an ergonomic position using the command console 200.

The console base 201 may include a central processing unit, a memory unit, a data bus, and associated data communication ports that are responsible for interpreting and processing signals such as camera imagery and tracking sensor data, e.g., from the instrument 115 shown in FIGS. 16A-16C. In some embodiments, both the console base 201 and the base 180 perform signal processing for load-balancing. The console base 201 may also process commands and instructions provided by the user 205 through the control modules 203 and 204. In addition to the keyboard 203 and joystick 204 shown in FIG. 17, the control modules may include other devices, for example, computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped or linked to an operation of the instrument (e.g., articulation, driving, water irrigation, etc.).

The displays 202 may include electronic monitors (e.g., LCD displays, LED displays, touch-sensitive displays), virtual reality viewing devices, e.g., goggles or glasses, and/or other display devices. In some embodiments, the display modules 202 are integrated with the control modules, for example, as a tablet device with a touchscreen. In some embodiments, one of the displays 202 can display a 3D model of the patient's luminal network and virtual navigation information (e.g., a virtual representation of the end of the endoscope within the model based on EM sensor position) while the other of the displays 202 can display image information received from the camera or another sensing device at the end of the instrument 115. In some implementations, the user 205 can both view data and input commands to the system 110 using the integrated displays 202 and control modules. The displays 202 can display 2D renderings of 3D images and/or 3D images using a stereoscopic device, e.g., a visor or goggles. The 3D images provide an "endo view" (i.e., endoscopic view), which is a computer 3D model illustrating the anatomy of a patient. The "endo view" provides a virtual environment of the patient's interior and an expected location of an instrument 115 inside the patient. A user 205 compares the "endo view" model to actual images captured by a camera to help mentally orient and confirm that the instrument 115 is in the correct—or approximately correct—location within the patient. The "endo view" provides information about anatomical structures, e.g., the shape of airways, circulatory vessels, or an intestine or colon of the patient, around the distal end of the instrument 115. The display modules 202 can simultaneously display the 3D model and CT scans of the anatomy the around distal end of the instrument 115. Further, the display modules 202 may overlay the already determined navigation paths of the instrument 115 on the 3D model and CT scans.

In some embodiments, a model of the instrument 115 is displayed with the 3D models to help indicate a status of a surgical procedure. For example, the CT scans identify a lesion in the anatomy where a biopsy may be necessary. During operation, the display modules 202 may show a reference image captured by the instrument 115 corresponding to the current location of the instrument 115. The display modules 202 may automatically display different views of the model of the instrument 115 depending on user settings and a particular surgical procedure. For example, the display modules 202 show an overhead fluoroscopic view of the instrument 115 during a navigation step as the instrument 115 approaches an operative region of a patient.

Figure 18:
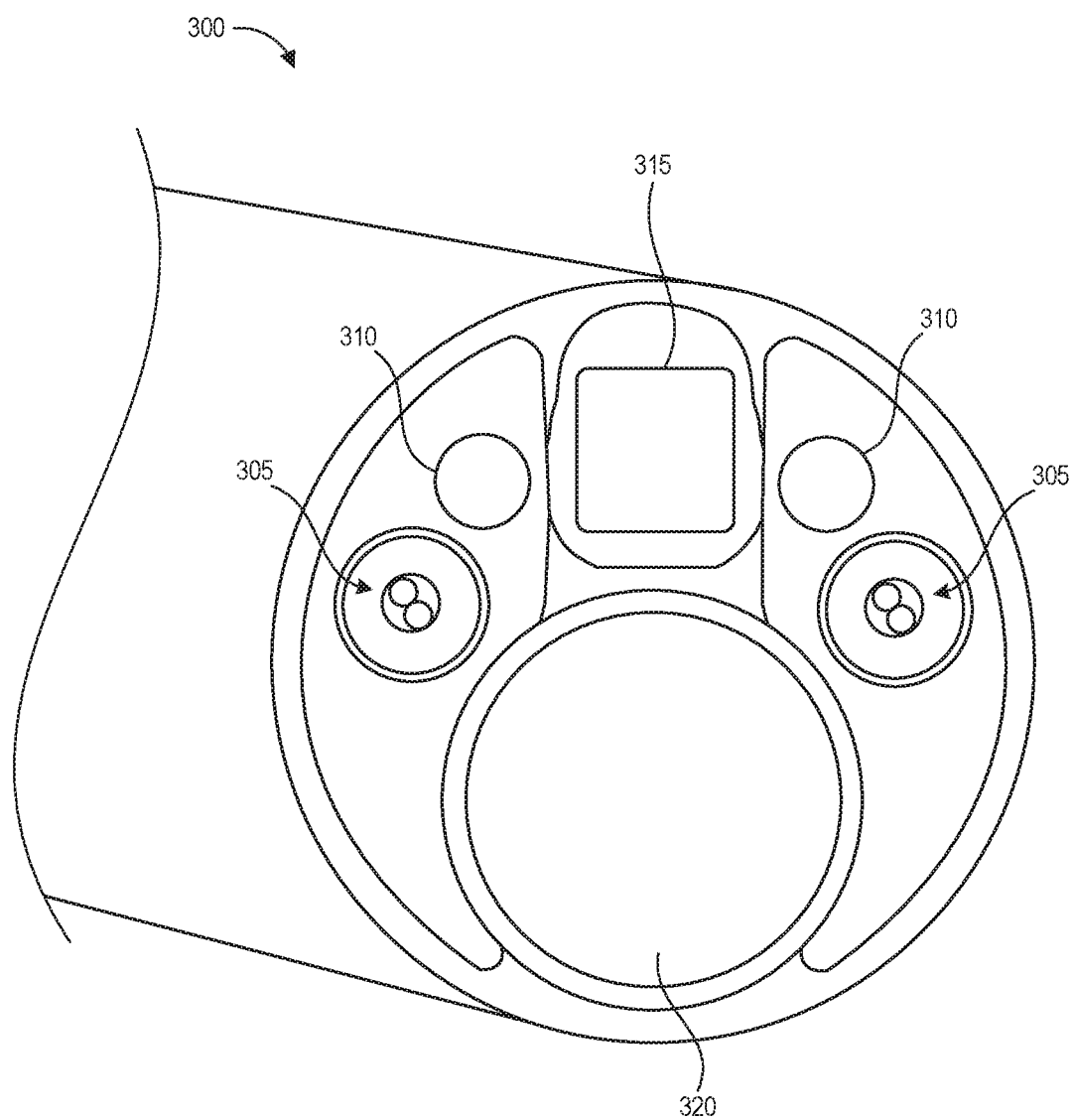
FIG. 18 illustrates the distal end of an example instrument having imaging and EM sensing capabilities as described herein, for example, the instrument of FIGS. 16A-16C.

FIG. 18 illustrates the distal end 300 of an example instrument having imaging and EM sensing capabilities as described herein, for example, the instrument 115 of FIGS. 16A-16C. In FIG. 18, the distal end 300 of the instrument includes an imaging device 315, illumination sources 310, and ends of EM sensor coils 305. The distal end 300 further includes an opening to a working channel 320 of the endoscope through which surgical instruments, such as biopsy needles, cytology brushes, and forceps, may be inserted along the endoscope shaft, allowing access to the area near the endoscope tip.

EM coils 305 located on the distal end 300 may be used with an EM tracking system to detect the position and orientation of the distal end 300 of the endoscope while it is disposed within an anatomical system. In some embodiments, the coils 305 may be angled to provide sensitivity to EM fields along different axes, giving the disclosed navigational systems the ability to measure a full 6 degrees of freedom: three positional and three angular. In other embodiments, only a single coil may be disposed on or within the distal end 300 with its axis oriented along the endoscope shaft of the instrument. Due to the rotational symmetry of such a system, it is insensitive to roll about its axis, so only 5 degrees of freedom may be detected in such an implementation.

B. Techniques for Location Sensor Registration.

As discussed above, location sensors may be used to track the location of a portion of an instrument (e.g., the distal end of the instrument) with respect to a model of an anatomy of a patient through which the instrument is driven during a medical procedure. It is to be appreciated that the model may be generated based on pre-operative measurements and the location sensor may function based on an independent coordinate system. In order to accurately determine the location of the instrument using the location sensors, the location sensor coordinate system is registered to the model coordinate system, which provides a transformation that can be applied to measurements from the location sensors to arrive at corresponding positions within the model coordinate system. FIG. 17 illustrates an example command console 200 that can be used, for example, as the command console 105 in the example operating environment 100. The command console 200 may include a console base 201, one or more display 202 (e.g., monitors), and one or more control modules (e.g., a keyboard 203 and joystick 204). In some embodiments, one or more of the command console 200 functionality may be integrated into a base 180 of the robotic system 110 or another system communicatively coupled to the robotic system 110. A user 205, e.g., a physician, remotely controls the robotic system 110 from an ergonomic position using the command console 200.

In certain implementations, the location sensor coordinate system can be registered to the model coordinate system based on location sensor data taken while the instrument is driven within the patient's anatomy. The amount and type of data required for registering the location sensor coordinate system to the coordinate system of the model of the anatomy may depend on the shape of a given anatomy. For example, one technique for registering a location sensor coordinate system to a model coordinate system involves maintaining a history of the data received from the location sensor(s) and matching the shape formed by the location data history to the candidate paths along which the instrument can travel based on the model of the anatomy. This technique may be more successful in finding a registration between the location sensor coordinate system and the model coordinate system for anatomies which have a certain amount of asymmetry.

Figure 19:
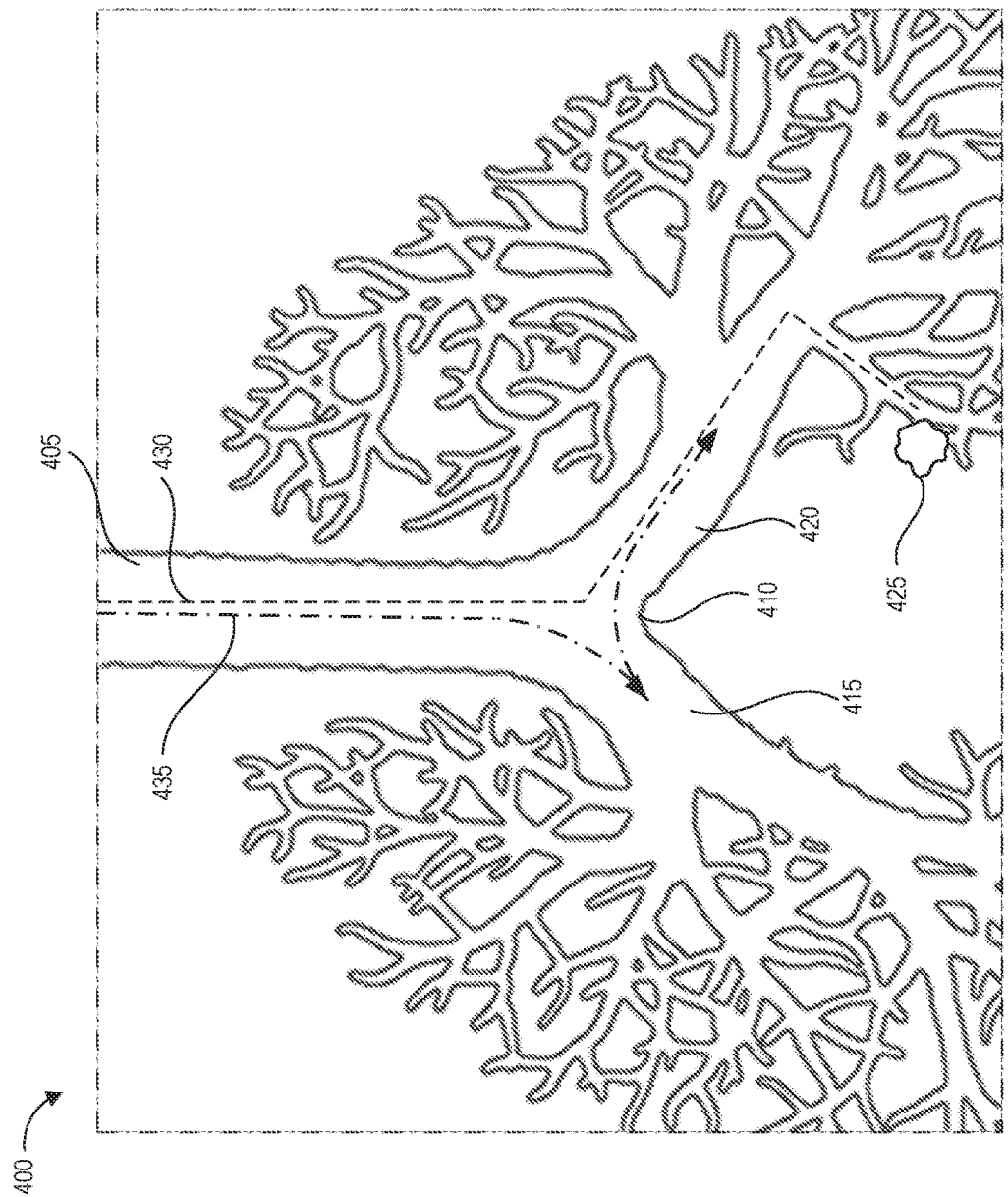
FIG. 19 illustrates an example luminal network in which location sensor registration can be performed in accordance with aspects of this disclosure.

FIG. 19 illustrates an example luminal network in which location sensor registration can be performed in accordance with aspects of this disclosure. In the embodiment of FIG. 19, the illustrated luminal network 400 corresponds to a patient's airway and includes a first-generation airway 405 (e.g., a trachea) which branches into two second-generation airways 415 and 420 (e.g., primary bronchi) at a main carina 410. Also illustrated is a target 425 (e.g., a lesion or nodule within the luminal network 400) to which the system may drive the instrument during a medical procedure. A target path 430 provides a planned route along which the instrument can be driven to reach the target 425. Depending on the embodiment, the system may automatically generate the target path 425 based on the pre-operatively scanned model of the luminal network 400 and the location of the target 425. In other embodiments, the target path 425 may be selected by a user during pre-operative planning. The system may display an illustration of the target path 430 with respect to the model on a display to provide the user with an indication of the direction in which to drive the instrument to reach the target 425. In certain embodiments, the target path 430 may include only a direct path to the target 425 which does not traverse the same portion of a luminal network more than once (i.e., traversing the target path 425 does not involve advancing down a segment of the luminal network and retracting the instrument back along the same segment).

As should be appreciated the airways defined by the second-generation branches 415 and 420 may not be symmetrical, but instead have different lengths and form different angles with the first-generation airway 405. In certain registration techniques in accordance with this disclosure, so called contra-lateral registration, leverage this asymmetry between the branches 415 and 420 to improve instrument registration. Embodiments can leverage the asymmetry by driving the instrument along a contra-lateral route 435, which may include driving the instrument into the second-generation airway 415 that is contra-lateral to the airway on the target path 430, retract back to the first-generation airway 405, and then drive to the second-generation airway on the path 430. As is discussed below, embodiments may additionally include features to facilitate the contra-lateral registration, such as automatically detecting the contra-lateral branch 415 and automatically determining when the distance traversed by the instrument along the contra-lateral branch 415 is sufficient.

To better explain the use of the contra-lateral route 435, the route or trace defined by the data output from the location sensors during the registration process (including the contra-lateral route 435) can be compared to the various shapes defined by the model of the luminal network 400. Due to the asymmetrical shape formed by the luminal network 400, the route defined by the location sensor data during the registration process may uniquely correspond to a single portion of the model of the luminal network 400, namely, the shape defined by the first-generation airway 405 and each of the second-generation airways 415 and 420. Thus, the registration between the location sensor coordinate system and the model coordinate system may be defined based on a transformation between the route or trace defined by the location sensor data (e.g., the contra-lateral route 435) during the registration process and the shape defined by the first-generation airway 405 and each of the second-generation airways 415 and 420.

Although FIG. 19 provides an example of a patient's airway as an embodiment of a luminal network, aspects of this disclosure may also apply to registration of location sensors used to navigate other luminal networks, and in particular, luminal networks which are at least partially asymmetric. For example, aspects of this disclosure may be applied to a gastro-intestinal network, a urinary tract, a vascular network, etc. Thus, aspects of this disclosure relate to the registration of location sensors based on location data received while driving an instrument along at least a portion of an asymmetrical route—within a luminal network.

Figure 20A:
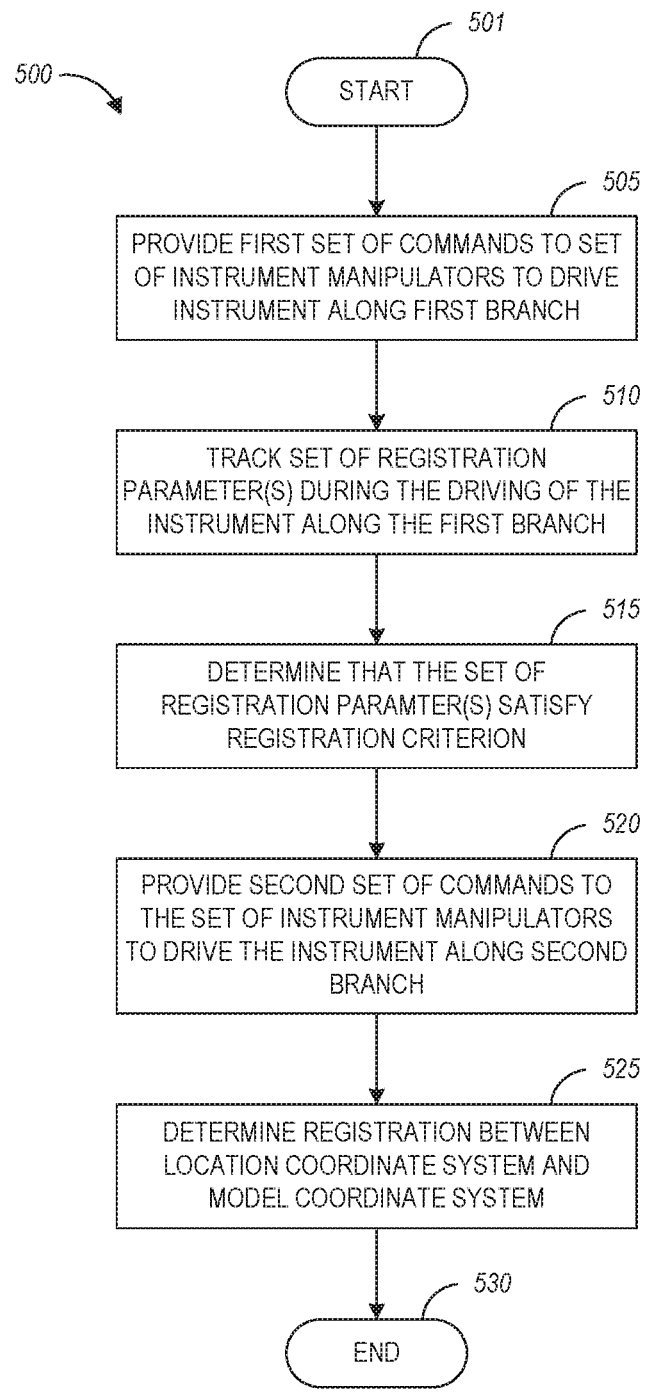
FIG. 20A is a flowchart illustrating an example method operable by a surgical robotic system, or component(s) thereof, for contra-laterally registering a location sensor coordinate system in accordance with aspects of this disclosure.

FIG. 20A is a flowchart illustrating an example method operable by a surgical robotic system, or component(s) thereof, for contra-laterally registering a location sensor coordinate system in accordance with aspects of this disclosure. It is to be appreciated that the steps of method 500 illustrated in FIG. 20A may be performed by a processor of a surgical robotic system. For convenience, the method 500 is described as performed by the processor of the system. When relevant to the description of the various steps of the method 500, reference will be made to the luminal network 400 illustrated in FIG. 19 to describe one embodiment of the method 500 below.

The processor may be included as a part of a system, including an instrument having a set of one or more location sensors. The set of location sensors may be configured to generate location data indicative of a position of the set of location sensors in a location sensor coordinate system. The location sensors may be located at or near a distal end of the instrument (e.g., see FIG. 18), and thus, the location data may be indicative of the location of the distal end of the instrument. The system may further include a set of instrument manipulators configured to control movement of the distal end of the instrument and at least one computer-readable memory in communication with the processor and having stored thereon a model of a luminal network of a patient. The model may include a target within a model coordinate system and a path to the target. The memory may further have stored thereon computer-executable instructions to cause the set of processors to perform the method 500.

The method 500 begins at block 501. At block 505, the processor provides a first set of commands to the set of instrument manipulators to drive the instrument along a first branch (e.g., a contra-lateral branch 415) of the luminal network. In some embodiments, the first set of command may be generated based on user input received from a set of one or more user input devices. Thus, the processor may cause user instructions to be provided to a user which include instructions to follow the set of movements associated with the registration process (e.g., to drive the instrument along a first portion of the contra-lateral registration route 435). The system may then receive the user input corresponding to the user instructions and generate the first set of command for movement of the instrument along the first branch. As illustrated in FIG. 19, first branch 415 is located outside of the target path 430 to the target 430. Thus, the first set of commands may cause the instrument manipulators to drive the instrument along the first portion of the contra-lateral registration route 435 down the contra-lateral branch 415.

At block 510, the processor tracks a set of one or more registration parameters during the driving of the instrument along the first branch. The registration parameters may be any data that can be tracked by the system and used to determine whether sufficient data has been collected by the system to perform registration between the location sensor coordinate system and the model coordinate system. At block 515, the processor determines that the set of registration parameters satisfy a registration criterion. The registration parameters satisfying the registration criterion may be indicative of the instrument travelling a sufficient distance along the contra-lateral branch 415 and the registration process can continue with the instrument being retracted back to the target path 430. A more detail embodiment for tracking the registration parameters and determining whether the registration parameters satisfy the registration criterion is provided below in connection with FIG. 20B.

At block 520, the processor provides a second set of commands to the set of instrument manipulators to return the instrument back to the target path 430 and to drive the instrument along a second branch (e.g., the lateral branch 420). As illustrated in FIG. 19, the branch 420 is located along the target path 430 to the target 425. The processor may drive the instrument along the remainder of the contra-lateral registration route 435, continuing down the lateral branch 420.

At block 525, the processor determines a registration between the location sensor coordinate system and the model coordinate system based on the location data received from the set of location sensors during the driving of the instrument along the first branch and the second branch (e.g., along the contra-lateral registration route 435). By confirming that the registration parameters satisfy the registration criterion in block 515 prior to providing the commands to retract the instrument back to the lateral branch 420, the processor can ensure that sufficient location data is collected to determine the registration. The method 500 ends at block 530.

In certain embodiments, the registration between the location sensor coordinate system and the model coordinate system may be further based on the first set of commands referenced in step 505 and the second set of commands from step 520. That is, the first and second sets of commands may be robot data which provided to the instrument manipulator(s) to control the movement of the instrument. Since the first and second sets of commands are used to control the movement of the instrument, the processor may be able to determine the location of the instrument when moved based on the first and second sets of commands. Thus, the processor may be able to determine the location of the distal end of the instrument with respect to the model based on the robot data used to drive the instrument. As an example, if the distal end of the instrument is located at or near the carina (see the carina 410 illustrated in FIG. 19) and positioned to drive down the first branch (e.g., the contra-lateral branch 415), after providing an insertion command to the instrument, the processor may determine that the distal end of the instrument has been inserted into the first branch by the amount instructed in the insertion command.

The processor may further be configured to generate the first and second sets of commands, provided to the instrument manipulator, based on user input received from a set of one or more user input devices. Thus, the driving of the instrument may be performed manually based on user input received by the system.

As discussed above, the registration may include a transformation that can map data from the location sensor coordinate system to the model coordinate system. The transformation may include a translation and/or a rotation that can be applied to location sensor data. To aid in determining the registration which correctly maps data from the location sensor coordinate system to the model coordinate system, the processor may identify a known location in each of the two coordinate systems which can be used as an anchor between the location sensor coordinate system and the model coordinate system. With reference to FIG. 19, the carina 410 can be automatically identified from the model of the luminal network and the user can easily navigate the instrument to the carina 410 and provide feedback to the processor indicative of the location of the carina 410.

In certain embodiments, the system may also generate guiding instructions to determine an anchor point at a known location in each of the location sensor and model coordinate systems. The guiding instructions may include instructions to the user to drive the distal end of the instrument to touch the carina 410 and then retract the instrument after touching the carina 410. Based on user input, the processor may provide commands to drive the instrument to the carina 410 and retract the instrument after reaching the carina 410. Thus, by identifying the location of the instrument just prior to the retraction, the processor can determine that the identified location within the location sensor coordinate system corresponds to the location of the carina 410. The location of the carina 410 in each of the two coordinate systems can then be used as once piece of data to determine the transformation mapping the location sensor coordinate system to the model coordinate system.

In another example embodiment, rather than requiring the user to indicate the location of the carina 410 by retracting the instrument, the processor may determine the location of the instrument with respect to the model using a camera included on the distal end of the instrument. The user may use images captured by the camera and provided to the display to navigate through the luminal network. In one embodiment, images obtained by the camera may be displayed to the user in real-time. The processor may be configured to determine a position of the distal end of the instrument based on an analysis of an image received from the camera. Any image processing technique that can determine the features of the interior of the luminal network may be used to determine the position of the distal end of the instrument with respect to the model. The processor may further determine that the distal end of the distal end of the instrument is within a threshold distance from the first location (e.g., the carina 410) based on determined position of the distal end of the instrument.

Figure 20B:
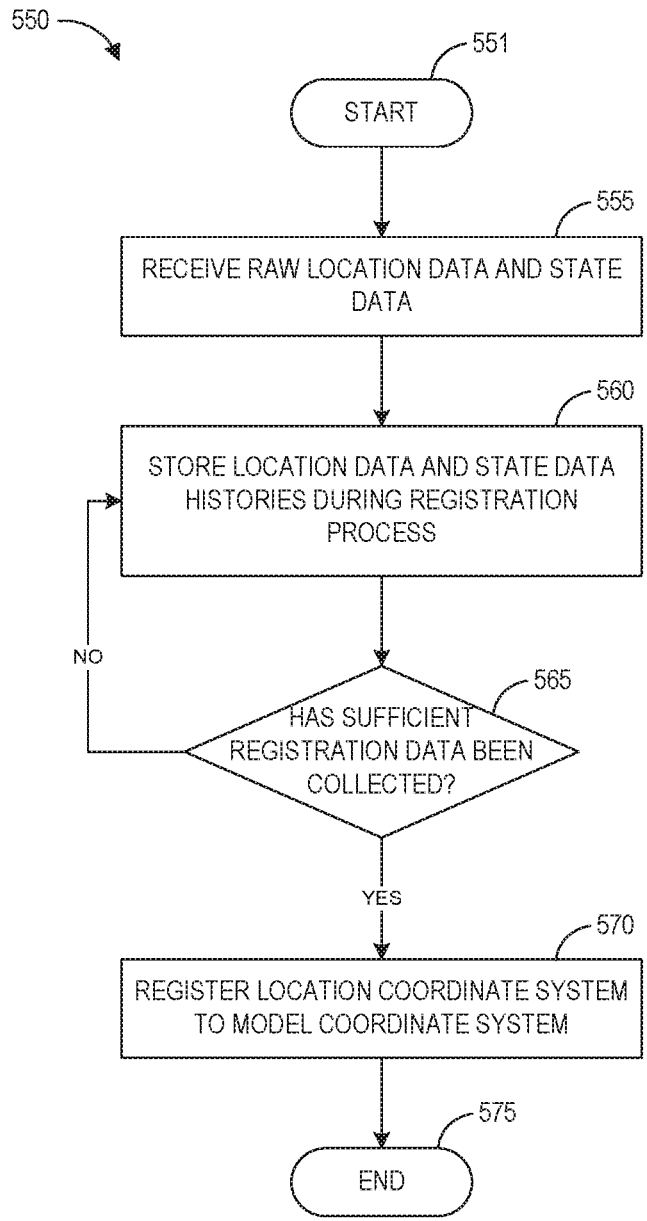
FIG. 20B is a flowchart illustrating an example method operable by a surgical robotic system, or component(s) thereof, for determining whether sufficient location data has been received to facilitate contra-lateral registration in accordance with aspects of this disclosure.

FIG. 20B is a flowchart illustrating an example method operable by a surgical robotic system, or component(s) thereof, for determining whether sufficient location data has been received to facilitate contra-lateral registration in accordance with aspects of this disclosure. It is to be appreciated that the steps of method 550 illustrated in FIG. 20A may be performed by a processor of a surgical robotic system. For convenience, the method 550 is described as performed by the processor of the system. The steps of method 550 may be performed as an implementation of block(s) 510 and 515 of FIG. 20A.

The method 550 begins at block 551. At block 555, the processor receives raw location data and state data. As used herein "raw location data" may refer to location data indicative of a location within the location sensor coordinate system. Thus, "raw location data" may be location data that is representative of a location within the instrument coordinate frame rather than the model coordinate frame. Prior to performing the registration process and determining a registration between the location sensor coordinate system and the model coordinate system, the processor cannot map the location sensor data to the model coordinate system. Thus, it will be appreciated that the location data received prior to the completion of the registration process is unregistered or raw location data.

The state data may refer to data produced by the processor which is indicative of the location of the instrument within the model. For example, the localization system 90 illustrated in FIG. 15 may be used to produce location data 96 (also referred to as state data), which can be used in the methods 500 and 550. The state data may include depth information, such as the current depth of the instrument in a given segment or an insertion depth within the anatomical model. The state data may also include an orientation of the distal end of the instrument in the model coordinate frame. In certain embodiments, the processor may receive the raw location data and state data throughout the registration process 500 illustrated in FIG. 20A.

At block 560, the processor may store the location data and state data collected during a registration process, such as the registration process performed via the method 500. The registration process may include a choreographed set of movements of the instrument which may be related to the shape of the luminal network. The set of movements may also be based on a defined target path 430 to a target 425 within the model. The registration process may involve providing a first set of commands to the set of instrument manipulators to drive the instrument along a first branch of the luminal network, where the first branch is on the contra-lateral branch 415 and, thus, outside of the target path 430 to the target 425. The registration process may also involve providing commands to bring the instrument back to and continue along the target path 430 to the target site 425. The choreographed set of movements may include the set(s) of commands required to drive the distal end of the instrument along the path defined by the contra-lateral registration route 435. The processor may track a set of one or more registration parameters during the driving of the instrument along the first branch, such as depth information.

At block 565, the processor may determine whether sufficient location sensor data has been collected as part of the contra-lateral phase of the registration process based on the registration parameters being tracked. In one embodiment, the processor may use registration parameters such as depth information (e.g., an insertion depth of the instrument) to determine whether the instrument has been driven a sufficient distance along the contra-lateral branch 415 of the contra-lateral route 435. In certain embodiments, after one registration criterion is satisfied, the processor may provide a second set of commands to the set of instrument manipulators to return the instrument back to the target path 430 and to drive the instrument towards the target site along a second branch. As the instrument continues along the target site, the processor may continue tracking the instrument location data and state data for the registration process.

By determining whether the instrument has been driven a sufficient distance along the contra-lateral branch 415, the system may be able to reduce the amount of input required from the user, thereby reducing the chances of user-error. For example, certain registration processes may require the user to drive to a plurality of defined locations and provide an input to the system indicating that the instrument has been driven to the defined locations. By eliminating this type of required user input, aspects of this disclosure can improve the ease of the registration process and reduce potential sources of user error.

At block 570, the processor may register the location coordinate system to the model coordinate system using the location data and state data tracked during the registration process (e.g., location data and state data tracked along the contra-lateral route 435 and the target path 430). As discussed above, this may include matching the shape of the path taken by the instrument as tracked using the location sensors to the shapes of the luminal network defined by the skeletal structure of the model. In certain embodiments, the shape of the model having the lowest difference from the tracked path is selected and used to determine a registration between the location sensor coordinate system and the model coordinate system. It is to be appreciated that because the tracked path includes the contra-lateral branch 415, embodiments may reduce the likelihood that the tracked path matches to other candidate paths in the model. The method 550 ends at block 575.

In determining the registration, the processor may be further configured to match the shapes defined by histories of the location sensor data and robot data. Thus, in certain implementations, the processor may be configured to generate a set of location data points representative of the location of the distal end of the instrument with respect to the location coordinate system while driving the instrument along the contra-lateral registration route. The processor may further generate a set of model points representative of the location of the distal end of the instrument with respect to the model coordinate system while driving the instrument along the contra-lateral registration route. The processor may generate the model points based on the history of robot data and the model. The two sets of points may be used by the processor to determine the registration between the location coordinate system and the model coordinate system is based on determining a registration which maps the set of location data points in the location coordinate system to the second set of model points in the model coordinate system.

Figure 21:
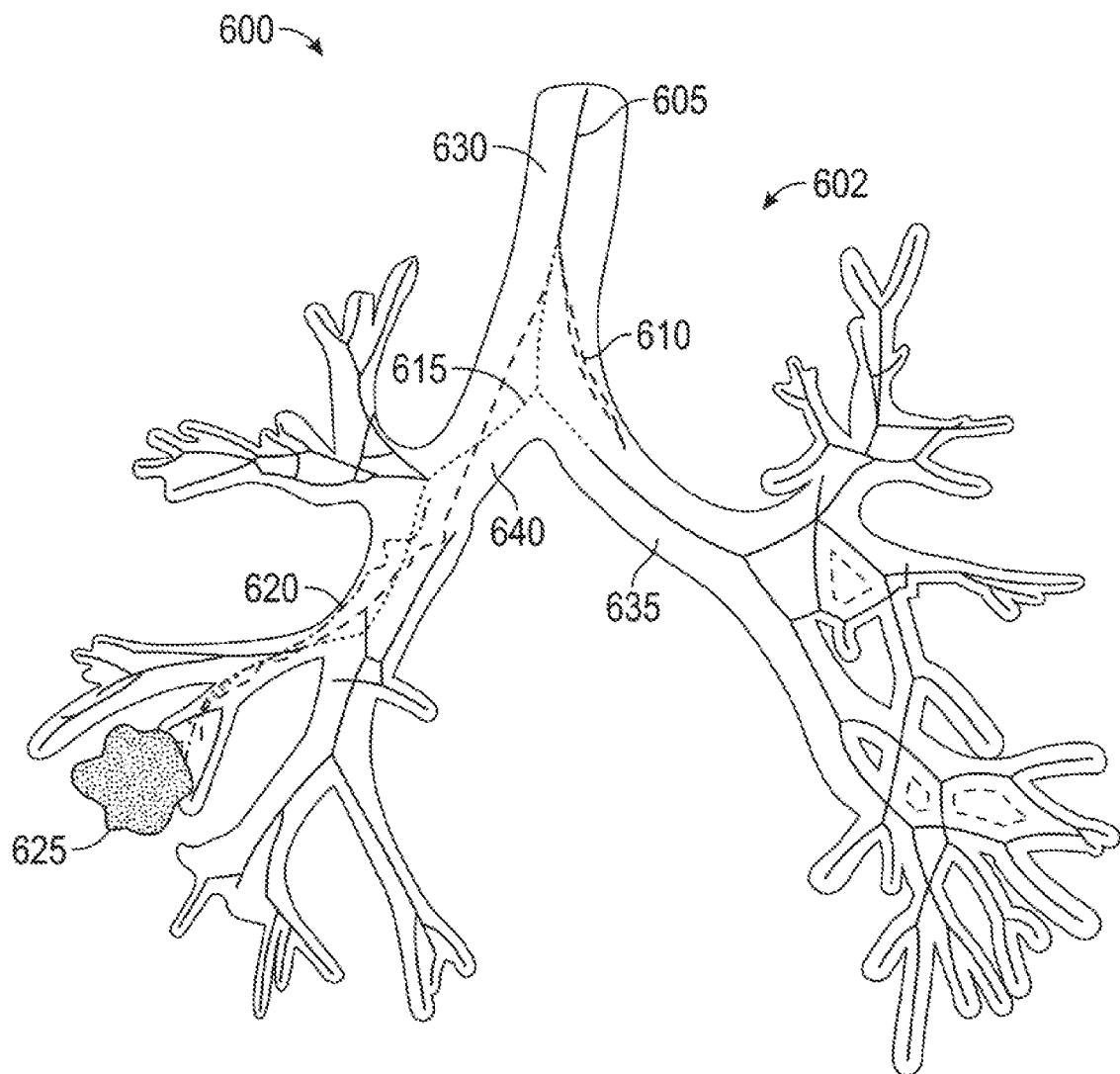
FIG. 21 is a diagram illustrating location data with respect to a model of a luminal network in accordance with aspects of this disclosure.

FIG. 21 is a diagram illustrating location data with respect to a model of a luminal network in accordance with aspects of this disclosure. In the example of FIG. 21, the diagram 600 includes model 602 of a pre-operative scan of the luminal network, which may also include a skeleton 605 defined by the midpoints along each of the airways defined by the model 602. In particular, the skeleton 605 includes a series of segments, each located at the midpoint of corresponding lumens in the luminal network. Also illustrated is ground truth data 610 representing the actual or true location of the distal end of the instrument during a contra-lateral registration process relative to the anatomy. The ground truth data 610 shown in FIG. 21 may have been generated by a testing tool that is not normally used during a procedure to highlight the accuracy of the contra-lateral registration process. In the illustrated example, a target 625 may be located on the left side of the figure. Accordingly, during a registration procedure, the instrument may be driven from the first-generation airway 630 into the contra-lateral second-generation airway 635. Thereafter, the instrument may be retracted back into the first-generation airway 630 and advanced into the lateral second-generation airway 640 located along a path to the target 625.

The system may also track the state data 615 representing the location of the instrument along the skeleton of the model 605. As discuss above, the processor may determine the state data based on data received from one or more different sources of data indicative of the location of the distal end of the instrument (e.g., via the localization module 95 of FIG. 15). Once sufficient data is received during the registration process, a registration transformation can be applied to the raw location data to generate registered location data 620. As shown in FIG. 21, the registered location data 620 may closely track the ground truth data 610. After the location data has been registered, the processor may use the registered location data 620 as an input in determining the state data 615.

Figure 22:
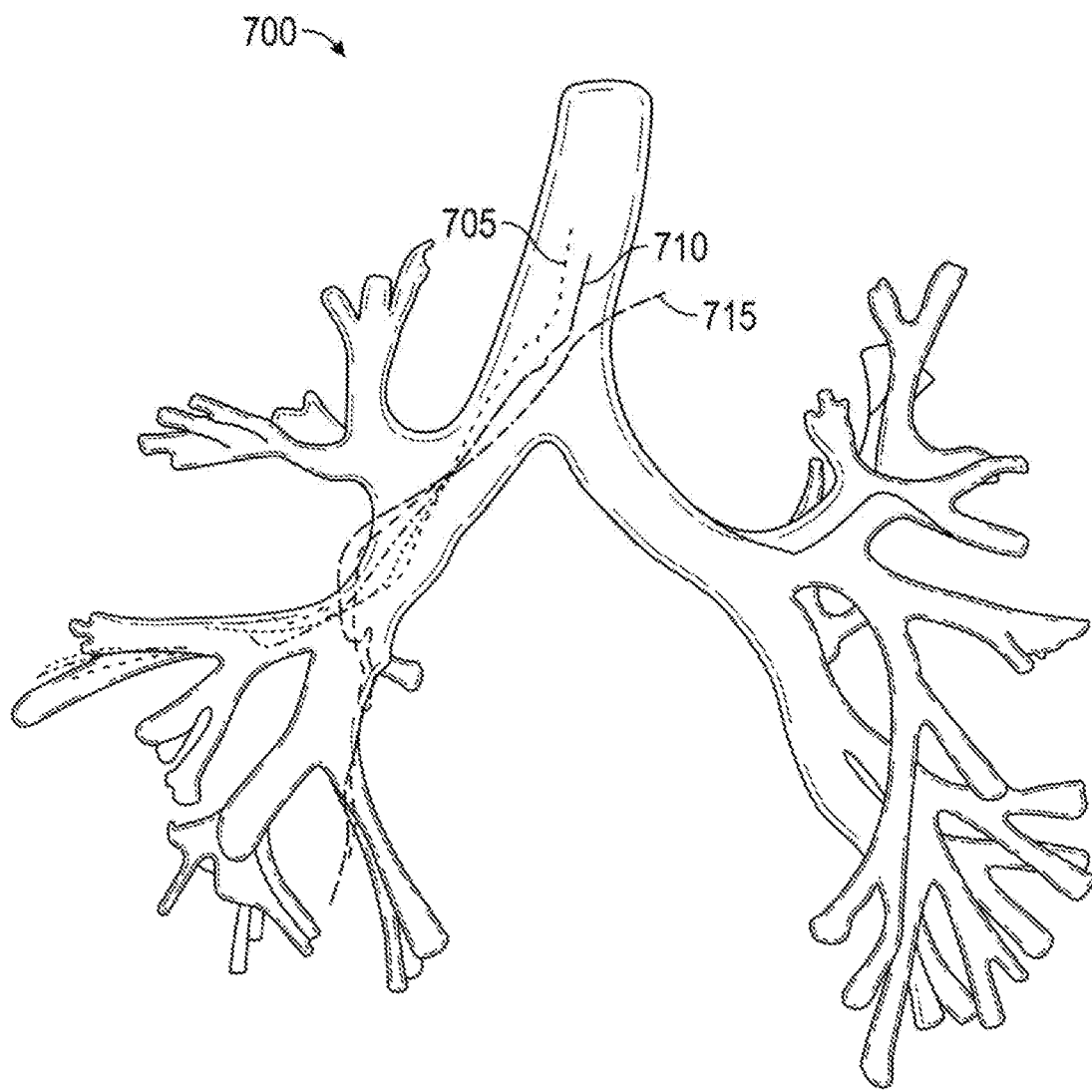
FIG. 22 is a diagram illustrating an example of registration of location data without preforming a contra-lateral registration process in accordance with aspects of this disclosure.

FIG. 22 is a diagram illustrating an example of registration of location data without preforming a contra-lateral registration process in accordance with aspects of this disclosure. In this example, when a contra-lateral registration process is not performed (e.g., the instrument is not driven down a contra-lateral branch) the raw location data 705 may substantially match two different candidate paths 710 and 715 within the model. That is, each of the two candidate paths 710 and 715 may have a similar shape such that a rotation and/or translation of the raw location data 705 may substantially match both paths 710 and 715. However, since the two paths 710 and 715 diverge, selecting the incorrect path 715 for registration may cause the location data to provide an incorrect indication of the location of the instrument when driven past the divergence between the two paths 710 and 715. In contrast, by performing a contra-lateral registration process in accordance with aspects of this disclosure, the incorrect candidate registration path 715 can be removed from the set of candidate registrations since a registration based on the incorrect candidate registration path 715 would not provide a match in shape along the contra-lateral route taken by the instrument (see, e.g., FIG. 21).

As discussed above, the contra-lateral registration procedure may provide a more accurate and more robust registration when the first branch and the second branch are asymmetrical (e.g., the second-generational segments). Thus, in certain embodiments, a processor may select an asymmetrical branching of the luminal network for the contra-lateral registration procedure. This selection of the location within the luminal network may also reduce the number of possible solutions to the matching between the location data and the model, leading to a more robust registration procedure. In the bronchoscopy example, driving the instrument into a contra-lateral branch before proceeding along the path to the target may provide sufficient raw location data to facilitate the registration of the location sensors to the model coordinate system. Accordingly, in certain embodiments, the first branch is located on a contra-lateral side of the luminal network with respect to the target.

C. Location Sensor Registration Planning.

Figure 23:
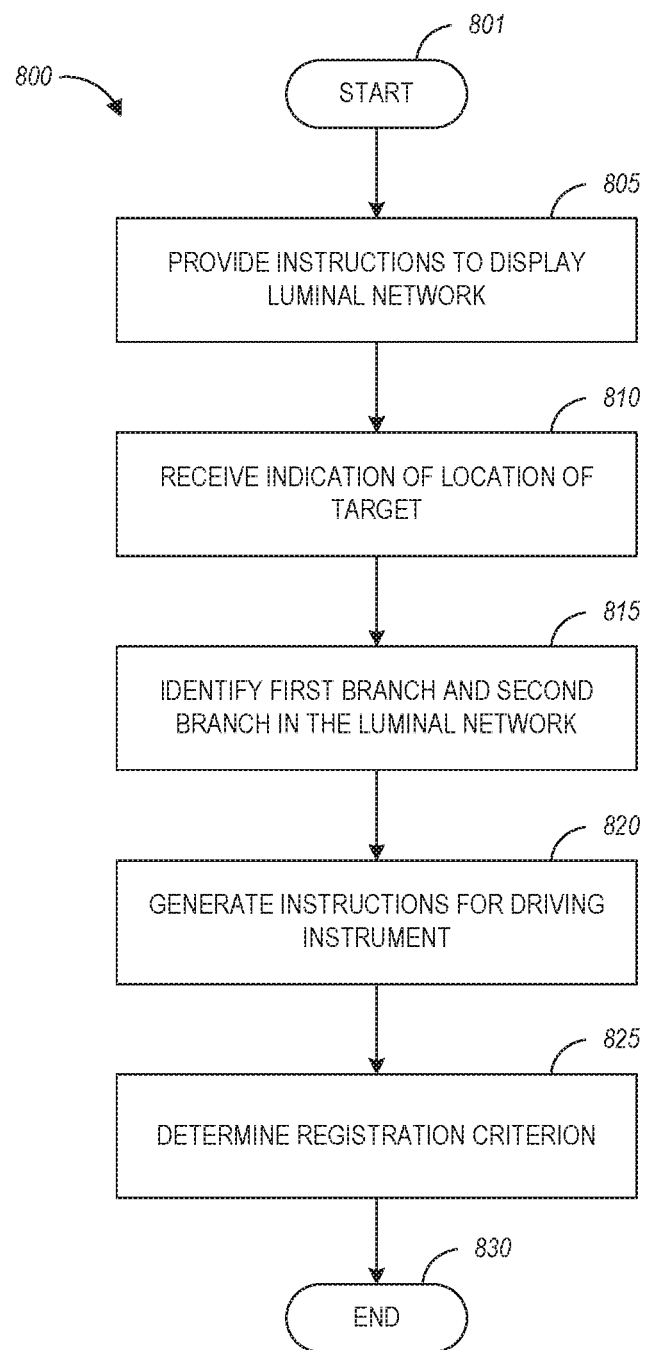
FIG. 23 is a flowchart illustrating an example method operable by a surgical robotic system, or component(s) thereof, for pre-operative planning in accordance with aspects of this disclosure.

Aspects of this disclosure also relate to pre-operative planning which may involve determining instructions and/or criterion related to a location sensor registration procedure. FIG. 23 is a flowchart illustrating an example method operable by a surgical robotic system, or component(s) thereof, for pre-operative planning in accordance with aspects of this disclosure. The procedure 800 for pre-operative planning may be operable by a surgical robotic system, or component(s) thereof, for pre-operative planning in accordance with aspects of this disclosure. For example, aspects of the method 800 for pre-operative planning may be performed by a command console, such as the command console 200 illustrated in FIG. 17 or may be performed by a processor (or a set of processors) of a surgical robotic system, which may be included as part of the command console. For convenience, the method for pre-operative planning is described as performed by the processor of the system. In certain embodiments, the system may also include at least one computer-readable memory in communication with the set of processors and having stored thereon a model of a luminal network of a patient. The model comprises a target within a model coordinate system and a path to the target. The memory may also store computer-executable instructions to cause the set of processors to perform the method 800.

The method 800 begins at block 801. At block 905, the processor provides instructions to display the luminal network via a display device. In particular, the processor may provide instructions to display the luminal network via a display device. This may involve, for example, the processor retrieving a model of the luminal network from the memory and displaying the model to be viewed by a user. The display of the model may involve displaying, for example, the skeleton and/or a more detailed segmented image generated based on preoperative scans of the luminal network (as shown in FIGS. 19, 21 and 22).

At block 810, the processor receives an indication of a location of a target within the model coordinate system. For example, the processor may receive an indication from a user, via a user input device, of a target portion of the model at which at least a portion of a medical procedure is to be performed. The target may be, for example, a desired location within the lung to biopsy lesions, stage lymph nodes, insert markers to guide radiotherapy or guide brachytherapy catheters. In other embodiments, the system can automatically detect or otherwise determine the target location 425 based on detecting features in the preoperative scan that are indicative of a tumor.

At block 815, the processor identifies a first branch (e.g., a branch located on a contra-lateral side of the luminal network, such as the contra-lateral branch 415 of FIG. 19) and a second branch (a branch located on the lateral side of the luminal network such as lateral branch 420 of FIG. 19) in the luminal network. Since the identified first and second branches are respectively located on the contra-lateral and lateral sides of the luminal network with respect to the location of the target, the first branch may be located outside of the path to the target and the second branch may be located along the path to the target.

In certain embodiments, based on the model and the selected target, the processor may automatically identify certain segments of the model which may be traversed by the instrument to aid in registration of the location sensors. This may include the processor identifying the first branch as a branch located on a contra-lateral side of the luminal network and the second branch as a branch located on a lateral side of the luminal network. In certain embodiments, the first and second branches may be second-generation branches of the luminal network, such as branches 415 and 420 illustrated in FIG. 19. The processor may further be configured to determine that the shape formed by the first and second branches is sufficiently unique within the luminal network such that, when the instrument is driven along a contra-lateral registration route defined by the second-generation branches, no other shape within the model will match the path taken by the instrument during the contra-lateral registration process. This determination may be performed by comparing the shape of the first and second branches with other possible shapes in the model to determine whether there exists any possible conflicts in shapes.

As discussed above, certain registration processes may require the user to drive the instrument to a plurality of defined locations within the luminal network and provide an indication to the system when the instrument is located at the defined locations. This technique may also require the user to identify the defined locations during a pre-operative planning stage. However, since the processor may automatically identify a contra-lateral route which can be used for the registration process, the necessary steps for the user during the pre-operative planning stage can be reduced.

At block 820, the processor generates a set of guiding instructions for driving the distal end of the instrument along the first branch, back to the path from the first branch, and along the second branch. Thus, the set of instructions may define a contra-lateral registration route, such as the contra-lateral registration route 435 of FIG. 19. The guiding instructions may be stored in memory to be provided to a user during the medical procedure. During the medical procedure, location data received from the set of one or more locations sensors during the driving of the instrument according to the instructions may facilitate a registration between the a location coordinate system of the location data and the model coordinate system. The registration may include at least one of a translation and a rotation between the location coordinate system and the model coordinate system. At block 825, the processor determines a registration criterion for one or more registration parameters tracked during the driving of the instrument along the first branch. The method 800 ends at block 830.

The registration criterion may relate to the amount of location data required for registration of the location sensor coordinate system to the model coordinate system. For example, the criterion may specify a required distance of travel for the instrument along the contra-lateral branch before the instrument can be returned back to the path from the first branch. The registration criterion may also depend on the specific shape of the patient's anatomy. For example, airways for some patients may have a larger discrepancy between the shapes and angles formed between the first and second branches than for other patients. When the differences between the first and second branches are more pronounced, it may not be necessary for the instrument to travel as far down the first branch to receive sufficient data for registration. In other embodiments, the registration criterion may be set based on a threshold determined to provide sufficient location data for registration for the majority of patients for the particular procedure which will be performed.

The registration parameters may include an insertion depth of the instrument into the contra-lateral branch. In this embodiment, the set of registration parameters satisfy the registration criterion in response to the insertion depth into the first branch being greater than a threshold insertion depth. For example, the registration criterion may include instructions to drive the instrument along at least 50% of the contra-lateral branch before returning to the first-generation branch on the path. The specific value may be different depending on the particular anatomy involved in the medical procedure and/or based on an analysis of the variation in the shapes of the anatomy in the general population.

Depending on the particular medical procedure, the processor may also determine whether the first branch and the second branch are asymmetrical. The processor may identify the first and second branches in response to determining that the first and second branches are asymmetrical. As discussed above, the registration process may be more accurate for asymmetrical paths and/or asymmetrically shaped luminal networks. Thus, the processor may select a bifurcation in the luminal network having an asymmetrical shape for the location at which the registration process is to be performed. In certain embodiments, such as for an airway, one branch at which the registration process can be performed is the branch from the trachea into the main bronchi. Thus, the processor may identify the first branch is further in response to determining that the first branch is located on a contra-lateral side of the luminal network with respect to the target.

In certain embodiments, the set of instructions include instructions to drive the instrument to a first location within the luminal network. The first location may be a location identifiable by the user during the medical procedure which can provide a known location within each of the location sensor coordinate system and the model coordinate system. For example, during a bronchoscopy procedure, the first location may correspond to the patient's carina. The carina may be identified within the model based on its location at the branch between the main bronchi and the user may be able to drive to the carina prior to the registration of the location data. In this embodiment, the first and second branches may correspond to main bronchi of the patient. The registration between the location sensor coordinate system and the model coordinate system may be further based on location data received from the set of location sensors while the distal end of the instrument is within a threshold distance from the first location. By using the first location as a known point of reference between the location coordinate system and the model coordinate system, the number of permutations for the registration can be limited. Additionally, the user instructions may include an instruction to retract the instrument after touching the carina. This retraction may be interpreted as an indication of the position of the carina, which can be used as the first location during the registration procedure.

3. Implementing Systems and Terminology

Implementations disclosed herein provide systems, methods and apparatuses for the registration of location sensors to a model coordinate system.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system, comprising:
   an instrument comprising a set of one or more location sensors, the set of one or more location sensors configured to generate location data indicative of a position of the set of one or more location sensors in a location sensor coordinate system;
   a set of instrument manipulators configured to control movement of a distal end of the instrument;
   a set of processors of a computer system; and
   at least one computer-readable memory of the computer system in communication with the set of processors and having stored thereon: (i) a model of a luminal network of a patient, the model comprising a target within a model coordinate system and a path to the target and (ii) a registration route comprising a first branch of the luminal network outside the path to the target and a second branch of the luminal network that is a part of the path to the target, the memory further having stored thereon computer-executable instructions to cause the set of processors to:
   provide a first set of commands to the set of instrument manipulators to drive the instrument along the first branch of the luminal network in accordance with the registration route,
   track a set of one or more registration parameters during the driving of the instrument along the first branch,
   determine that the set of one or more registration parameters satisfies a registration criterion,
   provide a second set of commands to the set of instrument manipulators to return the instrument back to the path and to drive the instrument along the second branch in accordance with the registration route, and
   determine a registration between the location sensor coordinate system and the model coordinate system based on the location data received from the set of one or more location sensors during the driving of the instrument along the first branch and the second branch.

2. The system of claim 1, wherein the registration comprises at least one of a translation and a rotation between the location coordinate system and the model coordinate system.

3. The system of claim 1, wherein the first branch and the second branch are asymmetrical.

4. The system of claim 1, wherein the first branch is located on a contra-lateral side of the luminal network with respect to the target.

5. The system of claim 1, wherein the registration between the location sensor coordinate system and the model coordinate system is further based on the first set of commands and the second set of commands.

6. The system of claim 1, further comprising:
   a set of one or more user input devices,
   wherein the memory further has stored thereon computer-executable instructions to cause the set of processors to generate the first set of commands and the second set of commands based on user input received from the one or more user input devices.

7. The system of claim 1, wherein the memory further has stored thereon computer-executable instructions to cause the set of processors to:
   provide a third set of commands to the set of instrument manipulators to drive the instrument to a first location within the luminal network,
   wherein the registration between the location sensor coordinate system and the model coordinate system is further based on the location data received from the set of one or more location sensors while the distal end of the instrument is within a threshold distance from the first location.

8. The system of claim 7, wherein the memory further has stored thereon computer-executable instructions to cause the set of processors to:
   provide a fourth set of commands to the set of instrument manipulators to retract the instrument after reaching the first location, and
   determine a position of the first location within the model coordinate system based on the third set of commands and the fourth set of commands,
   wherein the registration between the location sensor coordinate system and the model coordinate system is further based on the location data received prior to retracting the instrument from the first location.

9. The system of claim 7, wherein:
the instrument further comprises a camera,
wherein the memory further has stored thereon computer-executable instructions to cause the set of processors to:
 determine a position of the distal end of the instrument based on an analysis of an image received from the camera, and
 determine that the distal end of the distal end of the instrument is within a threshold distance from the first location based on determined position of the distal end of the instrument.

10. The system of claim 1, wherein the memory further has stored thereon computer-executable instructions to cause the set of processors to:
 generate a set of location data points representative of the location of the distal end of the instrument with respect to the location coordinate system while driving the instrument along the first branch and second branch, and
 generate a set of model points representative of the location of the distal end of the instrument with respect to the model coordinate system based on the first set of commands and the second set of commands,
 wherein the registration between the location coordinate system and the model coordinate system is further based on a mapping of the set of location data points in the location coordinate system to the set of model points in the model coordinate system.

11. The system of claim 1, wherein:
the set of one or more registration parameters comprises an insertion depth into the first branch,
the memory further has stored thereon computer-executable instructions to cause the set of processors to:
 determine that the set of registration parameters satisfies the registration criterion in response to the insertion depth into the first branch being greater than a threshold insertion depth.

12. A non-transitory computer readable storage medium having stored thereon instructions that, when executed, cause at least one computing device to:
 provide a first set of commands to a set of instrument manipulators to drive an instrument along a first branch of a luminal network, the instrument comprising a set of one or more location sensors, the set of one or more location sensors configured to generate location data indicative of a position of the set of one or more location sensors in a location sensor coordinate system, the set of instrument manipulators configured to control movement of a distal end of the instrument, a memory having stored thereon: (i) a model of a luminal network of a patient, the model comprising a target within a model coordinate system and a path to the target and (ii) a registration route comprising the first branch of the luminal network outside the path to the target and a second branch of the luminal network that is a part of the path to the target;
 track a set of one or more registration parameters during the driving of the instrument along the first branch in accordance with the registration route;
 determine that the set of one or more registration parameters satisfies a registration criterion;
 provide a second set of commands to the set of instrument manipulators to return the instrument back to the path and to drive the instrument along the second branch in accordance with the registration route; and
 determine a registration between the location sensor coordinate system and the model coordinate system based on the location data received from the set of one or more location sensors during the driving of the instrument along the first branch and the second branch.

13. The non-transitory computer readable storage medium of claim 12, wherein the registration comprises at least one of a translation and a rotation between the location coordinate system and the model coordinate system.

14. The non-transitory computer readable storage medium of claim 12, wherein the first branch and the second branch are asymmetrical.

15. The non-transitory computer readable storage medium of claim 12, wherein the first branch is located on a contra-lateral side of the luminal network with respect to the target.

16. The non-transitory computer readable storage medium of claim 12, wherein the registration between the location sensor coordinate system and the model coordinate system is further based on the first set of commands and the second set of commands.

17. The non-transitory computer readable storage medium of claim 12, further having stored thereon instructions that, when executed, cause at least one computing device to:
 generate the first set of commands and the second set of commands based on user input received from a set of one or more user input devices.

18. The non-transitory computer readable storage medium of claim 12, further having stored thereon instructions that, when executed, cause at least one computing device to:
 provide a third set of commands to the set of instrument manipulators to drive the instrument to a first location within the luminal network,
 wherein the registration between the location sensor coordinate system and the model coordinate system is further based on the location data received from the set of one or more location sensors while the distal end of the instrument is within a threshold distance from the first location.

19. The non-transitory computer readable storage medium of claim 18, further having stored thereon instructions that, when executed, cause at least one computing device to:
 provide a fourth set of commands to the set of instrument manipulators to retract the instrument after reaching the first location, and
 determine a position of the first location within the model coordinate system based on the third set of commands and the fourth of commands,
 wherein the registration between the location sensor coordinate system and the model coordinate system is further based on the location data received prior to retracting the instrument from the first location.

20. The non-transitory computer readable storage medium of claim 18, wherein:
the instrument further comprises a camera,
wherein the non-transitory computer readable storage medium further has stored thereon instructions that, when executed, cause at least one computing device to:
 determine a position of the distal end of the instrument based on an analysis of an image received from the camera, and
 determine that the distal end of the distal end of the instrument is within a threshold distance from the first location based on determined position of the distal end of the instrument.

21. The non-transitory computer readable storage medium of claim 12, further having stored thereon instructions that, when executed, cause at least one computing device to:

generate a set of location data points representative of the location of the distal end of the instrument with respect to the location coordinate system while driving the instrument along the first branch and second branch, and generate a set of model points representative of the location of the distal end of the instrument with respect to the model coordinate system based on the first set of commands and the second set of commands, wherein the registration between the location coordinate system and the model coordinate system is further based on a mapping of the set of location data points in the location coordinate system to the set of model points in the model coordinate system.

22. The non-transitory computer readable storage medium of claim 12, wherein:

the set of one or more registration parameters comprises an insertion depth into the first branch, wherein the non-transitory computer readable storage medium further has stored thereon instructions that, when executed, cause at least one computing device to:
determine that the set of registration parameters satisfies the registration criterion in response to the insertion depth into the first branch being greater than a threshold insertion depth.

23. A method of registering a set of one or more location sensors, comprising:

providing a first set of commands to a set of instrument manipulators to drive an instrument along a first branch of a luminal network, the instrument comprising the set of one or more location sensors, the set of one or more location sensors configured to generate location data indicative of a position of the set of one or more location sensors in a location sensor coordinate system, the set of instrument manipulators configured to control movement of a distal end of the instrument, a memory having stored thereon: (i) a model of a luminal network of a patient, the model comprising a target within a model coordinate system and a path to the target and (ii) a registration route comprising the first branch of the luminal network outside the path to the target and a second branch of the luminal network that is a part of the path to the target;

tracking a set of one or more registration parameters during the driving of the instrument along the first branch in accordance with the registration route;

determining that the set of one or more registration parameters satisfies a registration criterion, providing a second set of commands to the set of instrument manipulators to return the instrument back to the path and to drive the instrument along the second branch in accordance with the registration route; and determining a registration between the location sensor coordinate system and the model coordinate system based on the location data received from the set of one or more location sensors during the driving of the instrument along the first branch and the second branch.

24. The method of claim 23, wherein the registration comprises at least one of a translation and a rotation between the location coordinate system and the model coordinate system.

25. The method of claim 23, wherein the first branch and the second branch are asymmetrical.

26. The method of claim 23, wherein the first branch is located on a contra-lateral side of the luminal network with respect to the target.

27. The method of claim 23, wherein the registration between the location sensor coordinate system and the model coordinate system is further based on the first set of commands and the second set of commands.

28. The method of claim 23, further comprising:
generating the first set of commands and the second set of commands based on user input received from a set of one or more user input devices.

29. The method of claim 23, further comprising:
providing a third set of commands to the set of instrument manipulators to drive the instrument to a first location within the luminal network, wherein the registration between the location sensor coordinate system and the model coordinate system is further based on the location data received from the set of one or more location sensors while the distal end of the instrument is within a threshold distance from the first location.

30. The method of claim 29, further comprising:
providing a fourth set of commands to the set of instrument manipulators to retract the instrument after reaching the first location, and determining a position of the first location within the model coordinate system based on the third set of commands and the fourth of commands, wherein the registration between the location sensor coordinate system and the model coordinate system is further based on the location data received prior to retracting the instrument from the first location.

* * * * *